United States Patent
Kobayashi et al.

(10) Patent No.: US 8,481,275 B2
(45) Date of Patent: Jul. 9, 2013

(54) METHOD OF DETECTING PANCREATIC CANCER

(75) Inventors: Yuka Kobayashi, Tokyo (JP); Ken Kusama, Tokyo (JP); Masugu Kamei, Tokyo (JP)

(73) Assignee: J-Oil Mills, Inc., Tokyo (JP)

( * ) Notice: Subject to any disclaimer, the term of this patent is extended or adjusted under 35 U.S.C. 154(b) by 0 days.

(21) Appl. No.: 13/509,797

(22) PCT Filed: Jan. 17, 2011

(86) PCT No.: PCT/JP2011/050621
§ 371 (c)(1),
(2), (4) Date: May 15, 2012

(87) PCT Pub. No.: WO2011/089988
PCT Pub. Date: Jul. 28, 2011

(65) Prior Publication Data
US 2012/0244563 A1    Sep. 27, 2012

(30) Foreign Application Priority Data

Jan. 21, 2010 (JP) ................................ 2010-011447

(51) Int. Cl.
*G01N 33/53* (2006.01)
(52) U.S. Cl.
USPC .......................................... 435/7.1; 436/518
(58) Field of Classification Search
None
See application file for complete search history.

(56) References Cited

FOREIGN PATENT DOCUMENTS

JP    2009-168470    7/2009

OTHER PUBLICATIONS

Wimmerova et al. (J. Biol. Chem. 2003 vol. 278, p. 27059-67).*
Ai Tashiro et.al., "Purification and Characterization of a lectin from the fruiting body of *Stropharia rugosoannulata*", Japan, The Pharmaceutical Society of Japan / the Division of natural medicines, The Third Symposium on Pharmaceutical Food Science Abstracts, Oct. 21, 2009, vol. 3, p. 101-103.
Yasuo Oda, et.al., The Journal of Biological Chemistry, U.S.A, The American Society for Biochemistry and Molecular Biology, Inc., Aug. 2003, vol. 278/No. 34, 32439-32447.
http://pancreasmd.org/ed_blood.html, Dec. 19, 2012 (1 page).
N. Okuyama, "Fucosylated Haptoglobin is a Novel Marker for Pancreatic Cancer: A detailed analysis of the Oligosaccharide Structure and a Possible Mechanism for Fucosylation", Int. J. Cancer: 118, 2803-2808 (2006) 2005 Wiley-Liss, Inc., Osaka, Japan (6 pages).
M. Nakano, "Site Specific Analysis of N-glycans on Haptoglobin in Sera of Patients with Pancreatic Cancer: A Novel Approach for the Development of Tumor Markers", Int. J. Cancer: 122, 2301-2309, (2008) 2008 Wiley-Liss, Inc., Osaka, Japan (9 pages).
Biochemistry Dictionary, Ver. 3, edited by Kazutomo Imabori and Tamio Yamakawa, issued by Tokyo Kagaku Dojin, 1998, p. 521.

* cited by examiner

*Primary Examiner* — Jacob Cheu

(57) ABSTRACT

To provide a method of accurately detecting pathological haptoglobin using a lectin having strong affinity and high specificity for fucose. The method of the present invention for detecting pancreatic cancer is characterized in that a fucose α1→6 specific lectin is allowed to act on pathological haptoglobin contained in a sample obtained from a living body, said lectin: (1) being extractede from basidiomycetes, (2) having a molecular weight of 4,000 to 40,000 as determined by the SDS polyacrylamide gel electrophoresis, and (3) having affinity for a fucose α1→6 sugar chain with a binding constant of $1.0 \times 10^4$ $M^{-1}$ or more at 25° C.

16 Claims, 11 Drawing Sheets

PTL

LCA

AAL

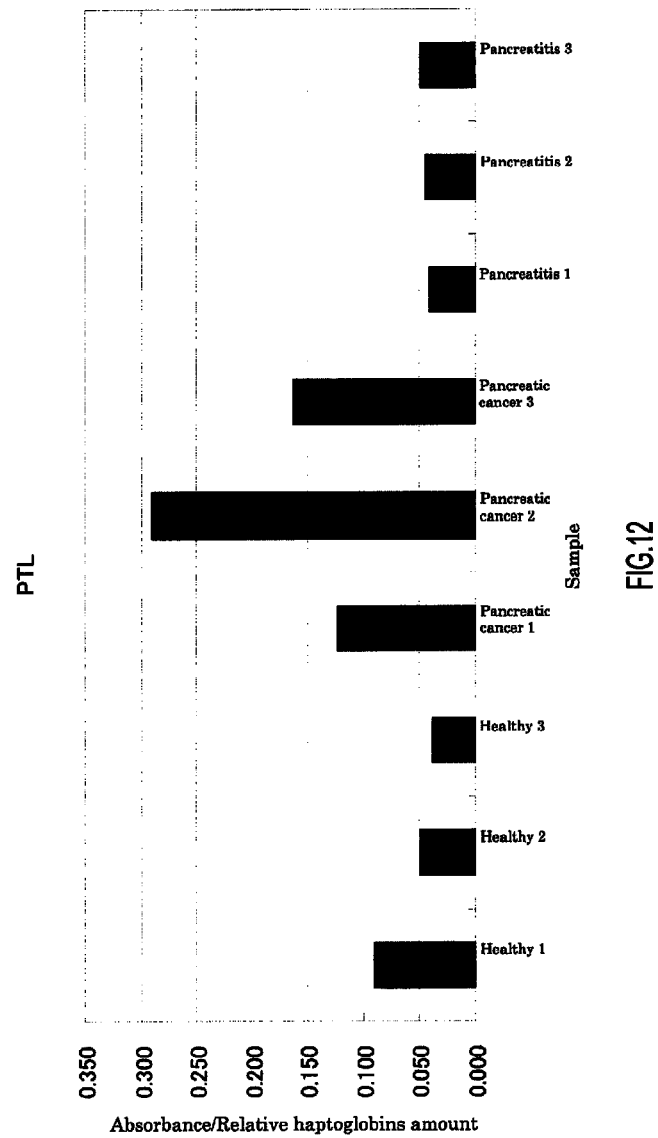

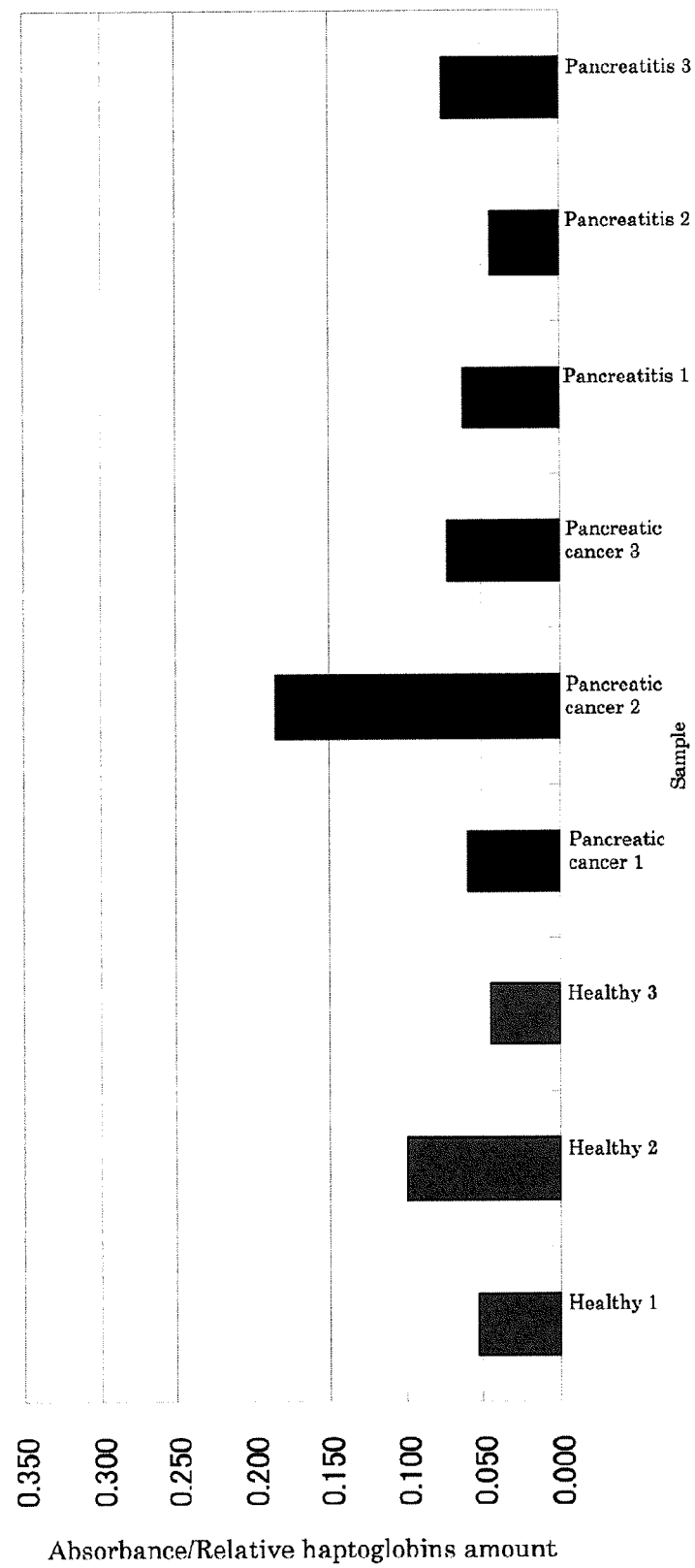

SEQUENCE LISTING

<160> NUMBER OF SEQ ID NOS: 6

<210> SEQ ID NO 1
<211> LENGTH: 8
<212> TYPE: PRT
<213> ORGANISM: Artificial sequence

```
<220> FEATURE:
<223> OTHER INFORMATION: common part of sequence No.2 to No.5
<220> FEATURE:
<221> NAME/KEY: MISC_FEATURE
<222> LOCATION: (4)..(4)
<223> OTHER INFORMATION: X stands for Asp/Asn/Glu/Thr.
<220> FEATURE:
<221> NAME/KEY: MISC_FEATURE
<222> LOCATION: (5)..(5)
<223> OTHER INFORMATION: X stands for Thr/Ser/Ala.
<220> FEATURE:
<221> NAME/KEY: MISC_FEATURE
<222> LOCATION: (6)..(6)
<223> OTHER INFORMATION: X stands for Tyr/Phe.
<220> FEATURE:
<221> NAME/KEY: MISC_FEATURE
<222> LOCATION: (7)..(7)
<223> OTHER INFORMATION: X stabds for Gln/Lys/Glu.

<400> SEQUENCE: 1

Cys Asp Gly Xaa Xaa Xaa Xaa Cys
1               5

<210> SEQ ID NO 2
<211> LENGTH: 40
<212> TYPE: PRT
<213> ORGANISM: Pholiota terrestris Overholts
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (17)..(17)
<223> OTHER INFORMATION: X stands for any amino acid, preferably Cys.
<220> FEATURE:
<221> NAME/KEY: MISC_FEATURE
<222> LOCATION: (20)..(20)
<223> OTHER INFORMATION: X stands for Tyr/Ser.
<220> FEATURE:
<221> NAME/KEY: MISC_FEATURE
<222> LOCATION: (23)..(23)
<223> OTHER INFORMATION: X stands for Phe/Tyr.
<220> FEATURE:
<221> NAME/KEY: MISC_FEATURE
<222> LOCATION: (27)..(27)
<223> OTHER INFORMATION: X stands for Arg/Lys/Asn.
<220> FEATURE:
<221> NAME/KEY: MISC_FEATURE
<222> LOCATION: (33)..(33)
<223> OTHER INFORMATION: X stands for Asp/Gly/Ser.
<220> FEATURE:
<221> NAME/KEY: MISC_FEATURE
<222> LOCATION: (35)..(35)
<223> OTHER INFORMATION: X stands for Asn/Ala.
<220> FEATURE:
<221> NAME/KEY: MISC_FEATURE
<222> LOCATION: (39)..(39)
<223> OTHER INFORMATION: X stands for Thr/Gln.

<400> SEQUENCE: 2

Ala Pro Val Pro Val Thr Lys Leu Val Xaa Asp Gly Asp Thr Tyr Lys
1               5                   10                  15

Xaa Thr Ala Xaa Leu Asp Xaa Gly Asp Gly Xaa Trp Val Ala Gln Thr
            20                  25                  30

Xaa Thr Xaa Val Phe His Xaa Gly
        35                  40

<210> SEQ ID NO 3
<211> LENGTH: 39
<212> TYPE: PRT
<213> ORGANISM: Stropharia rugosoannulata Farlow in Murr.
<220> FEATURE:
<221> NAME/KEY: MISC_FEATURE
```

```
<222> LOCATION: (4)..(4)
<223> OTHER INFORMATION: X stands for Pro/Gly.
<220> FEATURE:
<221> NAME/KEY: MISC_FEATURE
<222> LOCATION: (7)..(7)
<223> OTHER INFORMATION: X stands for Glu/Lys.
<220> FEATURE:
<221> NAME/KEY: MISC_FEATURE
<222> LOCATION: (9)..(9)
<223> OTHER INFORMATION: X stands for Val/Asp.
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (13)..(13)
<223> OTHER INFORMATION: X stands for Asn/Asp/Glu.
<220> FEATURE:
<221> NAME/KEY: MISC_FEATURE
<222> LOCATION: (17)..(17)
<223> OTHER INFORMATION: X stands for any amino acid, preferably Cys.
<220> FEATURE:
<221> NAME/KEY: MISC_FEATURE
<222> LOCATION: (20)..(20)
<223> OTHER INFORMATION: X stands for His/Ser.
<220> FEATURE:
<221> NAME/KEY: MISC_FEATURE
<222> LOCATION: (27)..(27)
<223> OTHER INFORMATION: X stands for Lys/His.
<220> FEATURE:
<221> NAME/KEY: MISC_FEATURE
<222> LOCATION: (29)..(29)
<223> OTHER INFORMATION: X stands for Val/Ile.
<220> FEATURE:
<221> NAME/KEY: MISC_FEATURE
<222> LOCATION: (33)..(33)
<223> OTHER INFORMATION: X stands for Gly/Asn/Ser.
<220> FEATURE:
<221> NAME/KEY: MISC_FEATURE
<222> LOCATION: (34)..(34)
<223> OTHER INFORMATION: X stands for Ala/Thr.
<220> FEATURE:
<221> NAME/KEY: MISC_FEATURE
<222> LOCATION: (39)..(39)
<223> OTHER INFORMATION: X stands for Arg/Thr.

<400> SEQUENCE: 3

Ala Pro Val Xaa Val Tyr Xaa Leu Xaa Xaa Asp Gly Xaa Ser Thr Lys
1               5                   10                  15

Xaa Thr Ala Xaa Leu Asp Tyr Gly Asp Gly Xaa Trp Xaa Ala Gln Trp
            20                  25                  30

Xaa Xaa Asn Val Phe His Xaa
        35

<210> SEQ ID NO 4
<211> LENGTH: 40
<212> TYPE: PRT
<213> ORGANISM: Lepista sordida (Schum. : Fr.) Sing.
<220> FEATURE:
<221> NAME/KEY: MISC_FEATURE
<222> LOCATION: (1)..(1)
<223> OTHER INFORMATION: X stands for Ala/Gln.
<220> FEATURE:
<221> NAME/KEY: MISC_FEATURE
<222> LOCATION: (4)..(4)
<223> OTHER INFORMATION: X stands for Pro/Lys.
<220> FEATURE:
<221> NAME/KEY: MISC_FEATURE
<222> LOCATION: (7)..(7)
<223> OTHER INFORMATION: X stands for Ala/Ser.
<220> FEATURE:
<221> NAME/KEY: MISC_FEATURE
<222> LOCATION: (8)..(8)
<223> OTHER INFORMATION: X stands for Met/Ile/Val.
<220> FEATURE:
```

```
<221> NAME/KEY: MISC_FEATURE
<222> LOCATION: (9)..(9)
<223> OTHER INFORMATION: X stands for Tyr/Thr.
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (13)..(13)
<223> OTHER INFORMATION: X stands for Asp/Asn.
<220> FEATURE:
<221> NAME/KEY: MISC_FEATURE
<222> LOCATION: (16)..(16)
<223> OTHER INFORMATION: X stands for Lys/Glu.
<220> FEATURE:
<221> NAME/KEY: MISC_FEATURE
<222> LOCATION: (17)..(17)
<223> OTHER INFORMATION: X stands for any amino acid, preferably Cys.
<220> FEATURE:
<221> NAME/KEY: MISC_FEATURE
<222> LOCATION: (20)..(20)
<223> OTHER INFORMATION: X stands for Ala/Asn.
<220> FEATURE:
<221> NAME/KEY: MISC_FEATURE
<222> LOCATION: (22)..(22)
<223> OTHER INFORMATION: X stands for Val/Asp/Asn.
<220> FEATURE:
<221> NAME/KEY: MISC_FEATURE
<222> LOCATION: (25)..(25)
<223> OTHER INFORMATION: X stands for Asp/Asn.
<220> FEATURE:
<221> NAME/KEY: MISC_FEATURE
<222> LOCATION: (27)..(27)
<223> OTHER INFORMATION: X stands for Arg/His/Asn.
<220> FEATURE:
<221> NAME/KEY: MISC_FEATURE
<222> LOCATION: (31)..(31)
<223> OTHER INFORMATION: X stands for Gln/Arg.
<220> FEATURE:
<221> NAME/KEY: MISC_FEATURE
<222> LOCATION: (34)..(34)
<223> OTHER INFORMATION: X stands for Thr/Val.

<400> SEQUENCE: 4

Xaa Asp Val Xaa Val Lys Xaa Xaa Xaa Asp Gly Xaa Thr Tyr Xaa
1               5                   10                  15

Xaa Thr Ala Xaa Leu Xaa Tyr Gly Xaa Gly Xaa Trp Val Ala Xaa Trp
            20                  25                  30

Ser Xaa Ala Val Phe His Gln Ser
        35                  40

<210> SEQ ID NO 5
<211> LENGTH: 39
<212> TYPE: PRT
<213> ORGANISM: Naematoloma sublateritium (Fr.) Karst/Hypholoma
      sublateritium(Fr.)Quel
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (13)..(13)
<223> OTHER INFORMATION: X stands for Asp/Thr.
<220> FEATURE:
<221> NAME/KEY: MISC_FEATURE
<222> LOCATION: (14)..(14)
<223> OTHER INFORMATION: X stands for Ser/Ala.
<220> FEATURE:
<221> NAME/KEY: MISC_FEATURE
<222> LOCATION: (16)..(16)
<223> OTHER INFORMATION: X stands for Gln/Lys.
<220> FEATURE:
<221> NAME/KEY: MISC_FEATURE
<222> LOCATION: (17)..(17)
```

-continued

```
<223> OTHER INFORMATION: X stands for any amino acid, preferably Cys.

<400> SEQUENCE: 5

Ala Pro Val Pro Val Thr Lys Leu Val Xaa Asp Gly Xaa Xaa Phe Xaa
1               5                   10                  15

Xaa Thr Ala Asn Leu Asp Phe Gly Asp Gly Asn Trp Val Ala Gln Trp
            20                  25                  30

Ser Thr Asn Val Phe His Asn
        35

<210> SEQ ID NO 6
<211> LENGTH: 40
<212> TYPE: PRT
<213> ORGANISM: Naematoloma sublateritium (Fr.) Karst/Hypholoma
      sublateritium(Fr.)Quel
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (14)..(14)
<223> OTHER INFORMATION: X stands for Asp/Thr.
<220> FEATURE:
<221> NAME/KEY: MISC_FEATURE
<222> LOCATION: (15)..(15)
<223> OTHER INFORMATION: X stands for Ser/Ala.
<220> FEATURE:
<221> NAME/KEY: MISC_FEATURE
<222> LOCATION: (17)..(17)
<223> OTHER INFORMATION: X stands for Gln/Lys.
<220> FEATURE:
<221> NAME/KEY: MISC_FEATURE
<222> LOCATION: (18)..(18)
<223> OTHER INFORMATION: X stands for any amino acid, preferably Cys.

<400> SEQUENCE: 6

Ala Pro Val Pro Val Thr Lys Leu Val Xaa Asp Asp Gly Xaa Xaa Phe
1               5                   10                  15

Xaa Xaa Thr Ala Asn Leu Asp Phe Gly Asp Gly Asn Trp Val Ala Gln
            20                  25                  30

Trp Ser Thr Asn Val Phe His Asn
        35                  40
```

METHOD OF DETECTING PANCREATIC CANCER

BACKGROUND OF THE INVENTION

1. Technical Field

The present invention relates to a method of detecting pancreatic cancer, and more particularly to a method of detecting pancreatic cancer in which pathological haptoglobin is used as a tumor marker.

2. Background Art

Since pancreas is located deep in the body, cancer is difficult to detect if it occurs in the pancreas. Tumor markers for diagnosing pancreatic cancer include CEA (the reference value: 5.0 ng/mL) and CA 19-9 (the reference value: 37 U/mL). False-positives may, however, be included in the results from these tumor markers, and therefore reliable results may not be obtained by using the tumor markers alone. In order to confirm pancreatic cancer, expensive thorough examinations, such as computerized tomography (CT), endoscopic retrograde cholangiopancreatography (ERCP), ultrasound endoscopy (EUS), angiography, etc. are required. Among these, ERCP and EUS are invasive and may impose a burden on patients.

Recent reports state that when pancreatic cancer is developed, fucose is attached to sugar chains of haptoglobin, one of glycoproteins (Non Patent Literatures 1 and 2, and Patent Literature 1). According to Non Patent Literature 1, this pathological haptoglobin is increased as the stage of pancreatic cancer progresses, and will disappear after the tumor site of pancreatic cancer is surgically removed.

Human haptoglobin is a glycoprotein comprised of 406 amino acids, containing four N-linked glycosylation sites on its β chain (molecular weight: 40,000). Human haptoglobin is abundant in serum of healthy adults at the concentration of 0.7 to 1.7 mg/mL. The use of pathological haptoglobin as a tumor marker for pancreatic cancer including early one can be achieved by accurately detecting pathological haptoglobin out of other haptoglobin molecules.

It is conceivable that a sugar binding "lectin" can be used to obtain the information about the changes in the structure and transfer of sugar chains on the cell surface associated with canceration. Conventionally, *Aleuria aurantia* lectin (AAL), *Lens culinaris* lectin (LCA), *Lotus japonicus* lectin (Lotus), *Ulex europaeus* lectin (UEA-I), etc. are known as lectins for detecting fucose. However, detection methods that use these conventional lectins often fail to exhibit a significant difference between healthy subjects and patients with pancreatic cancer.

Citation List
Patent Literature

Patent Literature 1: Japanese unexamined patent application publication No. 2009-168470

Non Patent Literature

Non Patent Literature 1: Fucosylated haptoglobin is a novel marker for pancreatic cancer: a detailed analysis of the oligosaccharide structure and a possible mechanism for fucosylation". Okuyama N, et. al., Int J Cancer. 2006 Jun. 1; 118 (11): 2803-8

Non Patent Literature 2: Site-specific analysis of N-glycans on haptoglobin in sera of patients with pancreatic cancer: a novel approach for the development of tumor markers". Nakano M, et. al., Int J Cancer. 2008 May 15; 122 (10): 2301-9

SUMMARY OF INVENTION

Technical Problem

An object of the present invention is to provide a method of accurately detecting pathological haptoglobin, wherein a lectin that specifically binds to pathological haptoglobin is used.

Solution to Problem

After extensive studies, the present inventors have found that the object can be achieved by the following invention(s). The present invention provides a method of detecting pancreatic cancer, wherein a fucose α1→6 specific lectin is allowed to act on pathological haptoglobin present in a sample obtained from a living body, with said lectin:

(1) being extracted from basidiomycetes,
(2) having a molecular weight of 4,000 to 40,000 as determined by the sodium dodecyl sulfate polyacrylamide gel electrophoresis (hereafter referred to as the SDS polyacrylamide gel electrophoresis), and
(3) having affinity for fucose α1→6 sugar chains with a binding constant of $1.0 \times 10^4$ $M^{-1}$ or greater at 25° C.

In addition, the fucose α1→6 specific lectin preferably (4) does not substantially bind to a high mannose sugar chain and/or a glycolipid having no α1→6 sugar chain.

The basidiomycete preferably belongs to the Strophariaceae, Tricholomataceae, Amanitaceae or Polyporaceae family. In particular, the basidiomycete is *Pholiota terrestris* Overholt, *Pholiota squarrosa, Pholiota aurivella, Stropharia rugosoannulata, Naematoloma sublateritium, Lepista sordida* or *Amanita muscaria*.

The sample is, for example, human serum or plasma.

In particular, the method of the present invention for detecting pancreatic cancer preferably detects pathological haptoglobin by an assay in which the fucose α1→6 specific lectin and anti-haptoglobin antibody are used.

The fucose α1→6 specific lectin is preferably labeled.

Furthermore, a method of distinguishing pancreatic cancer from pancreatitis is provided in which the fucose α1→6 specific lectin is allowed to act on pathological haptoglobin contained in a sample obtained from a living body having 30 U/mL or more of a tumor marker CA 19-9 in serum. The amount of CA 19-9 in serum is more preferably 32 U/mL or more, and even more preferably 35 U/mL or more. Accordingly, a healthy subject, a patient with pancreatic cancer and a patient with pancreatitis can be clearly distinguished.

The present invention provides a diagnostic reagent or kit for detecting pancreatic cancer and/or pancreatitis, comprising a fucose α1→6 specific lectin, the lectin:

(1) being extracted from basidiomycetes,
(2) having a molecular weight of 4,000 to 40,000 as determined by the SDS polyacrylamide gel electrophoresis, and
(3) having affinity for fucose α1→6 sugar chains with a binding constant of $1.0 \times 10^4$ $M^{-1}$ or greater at 25° C. Preferably, the kit comprises anti-haptoglobin antibody and/or anti-CA 19-9 antibody.

Advantageous Effects of Invention

The method for detecting pancreatic cancer of the present invention can detect pathological haptoglobin more accurately than the conventional fucose specific lectins. Pathological haptoglobin is expected to serve as a tumor marker for pancreatic cancer. As a result, pancreatic cancer, previously difficult to find, may be more easily detected. In particular, the method of the present invention is superior in convenience because it is applicable for cancer screening where serum is used. Furthermore, according to an assay where a fucose α1→6 specific lectin of the present invention and anti-haptoglobin antibody are used, rapid and simple detection of pancreatic cancer is possible. Pancreatic cancer and pancreatitis are difficult to distinguish by using a conventional tumor marker CA 19-9 alone. On the other hand, in the method of the present invention, pancreatic cancer and pancreatitis can be easily distinguished by the combined use of a fucose α1→6 specific lectin and CA 19-9.

BRIEF DESCRIPTION OF DRAWINGS

FIG. 12 shows the values calculated from dividing the PTL reaction values in FIG. 8 by the corresponding relative amount of haptoglobins in FIG. 11.

FIG. 13 shows the values calculated from dividing the AAL reaction values in FIG. 9 by the corresponding relative amount of haptoglobins in FIG. 11.

DESCRIPTION OF EMBODIMENTS

Figure 1:
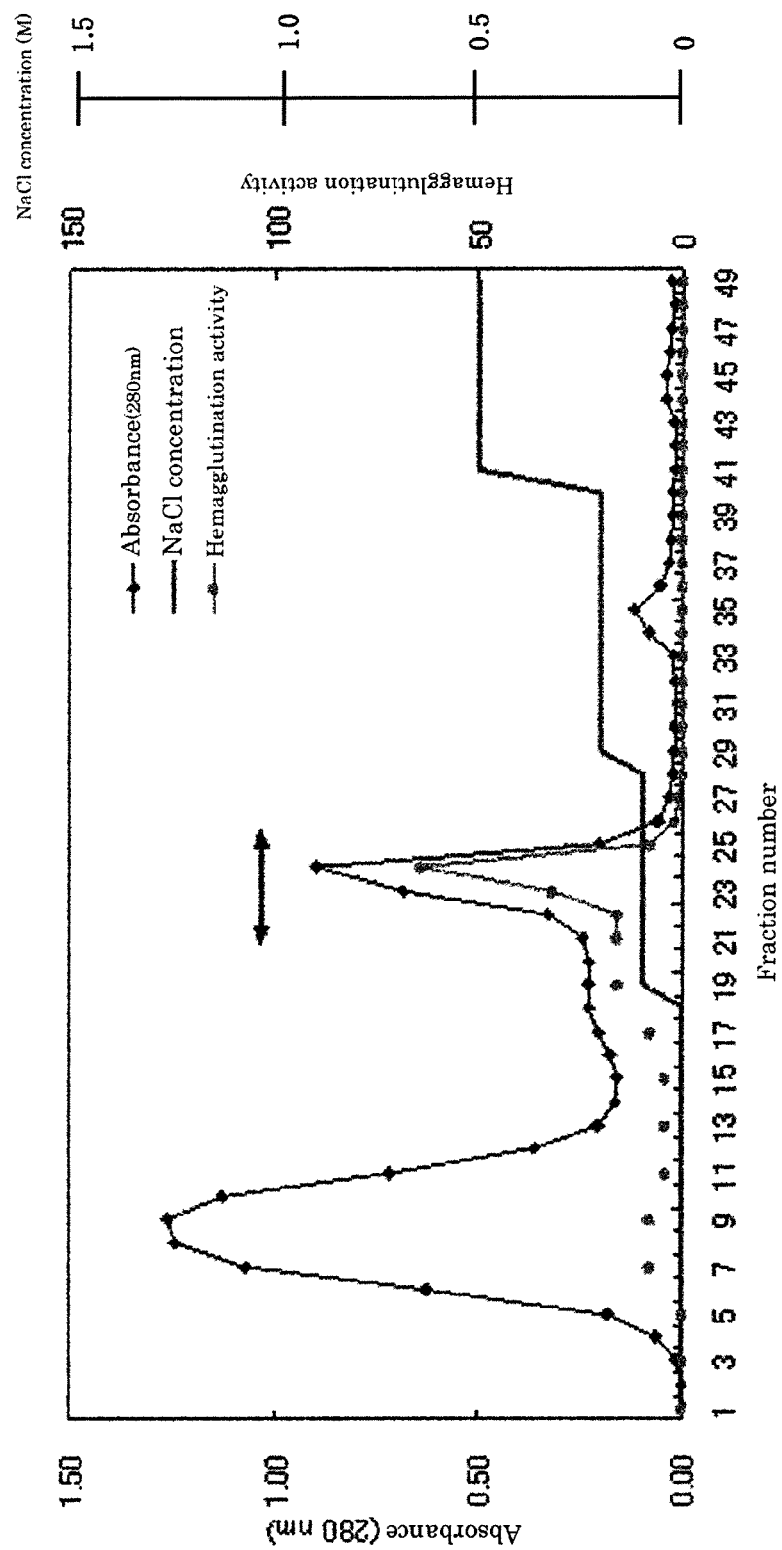
FIG. 1 shows an elution profile of ion exchange chromatography for PTL in Example of Preparation 1.

An embodiment of the method of the present invention for detecting pancreatic cancer will be described below in detail. The method of the present invention can be characterized by allowing a fucose α1→6 specific lectin having the following physical properties:
(1) being extracted from basidiomycetes,
(2) having a molecular weight of 4,000 to 40,000 as determined by the SDS polyacrylamide gel electrophoresis, and
(3) having affinity for fucose α1→6 sugar chains with a binding constant of $1.0 \times 10^4$ $M^{-1}$ or greater at 25° C., to act on pathological haptoglobin contained in a sample obtained from a living body, thereby detecting the pathological haptoglobin.

The detection method of the present invention requires the use of a lectin which specifically recognizes a fucose α1→6 linkage shown in the following formula.

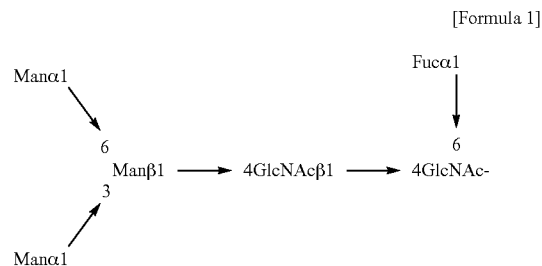

[Formula 1]

wherein Man represents mannose, GlcNAc represents N-acetyl glucosamine and Fuc represents fucose.

Using the novel fucose α1→6 specific lectin found by the present inventors, pancreatic cancer can be easily detected. The physical and chemical properties of the lectin will be described below in detail.
(1) The Origin of the Lectin The source of the fucose α1→6 specific lectin may be basidiomycetes. Among basidiomycetes, the lectin preferably belongs to the Strophariaceae, Tricholomataceae, Polyporaceae and Amanitaceae family. Strophariaceae includes *Pholiota terrestris* Overholts, *Stropharia rugosoannulata*, *Naematoloma sublateritium*, *Pholiota squarrosa*, *Pholiota aurivella* and *Pholiota adiposa*. Tricholomataceae includes *Lepista sordida*. Polyporaceae includes *Trichaptum elongatum* and *Microporus vernicipes*. Amanitaceae includes *Amanita muscaria*. In view of the recognition specificity of the lectin for a fucose α1→6 sugar-chain and the purification efficiency of the lectin, among these basidiomycetes, Strophariaceae, Tricholomataceae, or Amanitaceae are particularly preferred, and more preferred are *Pholiota terrestris* Overholts, *Pholiota squarrosa*, *Pholiota aurivella*, *Stropharia rugosoannulata*, *Naematoloma sublateritium*, *Lepista sordida* or *Amanita muscaria*.
(2) The Molecular Weight of the Lectin The molecular weight of the fucose α1→6 specific lectin is 4,000 to 40,000, preferably 4,000 to 20,000 as determined by the SDS polyacrylamide gel electrophoresis. The molecular weight herein by the SDS polyacrylamide gel electrophoresis was determined, for example, according to the Laemmi method (Nature, 227: 680, 1976).
(3) The Binding Constant of the Lectin The binding constant of the fucose α1→6 specific lectin for fucose α1→6 sugar chains is $1.0 \times 10^4$ $M^{-1}$ or greater, preferably $1.0 \times 10^5$ $M^{-1}$ or greater, and more preferably $1.0 \times 10^6$ $M^{-1}$ or greater. That is, it is significantly higher than that of AAL, *Aspergillus* lectins (AOL), LCA, *Daffodil* lectins (NPA) and *Pisum sativum* lectins (PSA) which are previously known to have affinity for fucose α1→6. This means that the fucose α1→6 specific lectin binds to a fucose α1→6 sugar chain with extremely high selectivity compared with the conventional lectins.

The above binding constants can be measured, for example, by the frontal affinity chromatography (FAC) method. The FAC method is described in detail, for example, in PCT/JP2009/003346. PCT/JP2009/003346 is incorporated herein by reference.

Fucose α1→6 sugar chains may have sialic acid at the non-reducing end. The conventional fucose α1→6 specific lectins (for example, LCA, NPA and PSA) showed lower affinity for fucose α1→6 sugar chains having sialic acid at the non-reducing terminal thereof. On the other hand, the fucose α1→6 specific lectin is superior to the conventional ones in that it also shows higher affinity for such sugar chains.

(4) Sugar Binding Specificity of the Lectin

The fucose α1→6 specific lectin preferably does not substantially bind to a high mannose sugar chain and/or a glycolipid having no fucose α1→6 sugar chain. This provides the fucose α1→6 specific lectin with even higher binding specificity. As used herein, "do not substantially bind to" means that a binding constant is $1.0 \times 10^3$ $M^{-1}$ or less, preferably $1.0 \times 10^2$ $M^{-1}$ or less, and in particular preferably 0.

As used herein, a "high mannose type sugar chain" refers to one of the subgroups of asparagine-linked sugar chains, which is a collective term of sugar chains having $Man_5$-GlcNAc-GlcNAc as a mother core and 0-4 α mannosyl residues bound to the α-mannosyl residue at a non-reducing end via α1-2 linkages.

(5) Binding of the Lectin to a Branched Chain

The fucose α1→6 specific lectin preferably has affinity for a mono-, bi-, tri- and/or tetra-antennary sugar chain having a fucose α1→6 N-linkage with a binding constant of $1.0 \times 10^4$ $M^{-1}$ or more at 25° C., and more preferably a binding constant of $1.0 \times 10^5$ $M^{-1}$ or more.

(6) Amino Acid Sequence of the Lectin

The fucose α1→6 specific lectins have the amino acid structure shown in SEQ ID No: 1 in Table 1 in common. Xaa at the positions 4, 5, 6 and 7 of SEQ ID No: 1 represent Asp/Asn/Glu/Thr, Thr/Ser/Ala, Tyr/Phe and Gln/Lys/Glu, respectively, wherein the slash marks means "or."

Specific examples of the fucose α1→6 specific lectin which can be used in the method of the present invention are shown in SEQ ID Nos: 2-6. The lectin shown in SEQ ID No: 2 is a novel lectin having a molecular weight of 4,500 which can be extracted from *Pholiota terrestris* Overholts (PTL). Xaa at positions 10 and 17 of SEQ ID No: 2 may be any amino acid residues, while they are preferably Cys. Xaa at positions 20, 23, 27, 33, 35 and 39 are Tyr/Ser, Phe/Tyr, Arg/Lys/Asn, Asp/Gly/Ser, Asn/Ala and Thr/Gln, respectively.

The lectin shown in SEQ ID No: 3 is a novel lectin having a molecular weight of 4,500 which can be extracted from *Stropharia rugosoannulata* (SRL). Xaa at positions 10 and 17 of SEQ ID No: 3 may be any amino acid residues, while they are preferably Cys. Xaa at positions 4, 7, 9, 13, 20, 27, 29, 33, 34 and 39 are Pro/Gly, Glu/Lys, Val/Asp, Asn/Asp/Glu, His/Ser, Lys/His, Val/Ile, Gly/Asn/Ser, Ala/Thr and Arg/Thr, respectively.

The lectin shown in SEQ ID No: 4 is a novel lectin having a molecular weight of 4,500 which can be extracted from *Lepista sordida* (LSL). Xaa at positions 10 and 17 of SEQ ID No: 4 may be any amino acid residues, while they are preferably Cys. Xaa at positions 1, 4, 7, 8, 9, 13, 16, 20, 22, 25, 27, 31 and 34 are Ala/Gln, Pro/Lys, Ala/Ser, Met/Ile/Val, Tyr/Thr, Asp/Asn, Lys/Glu, Ala/Asn, Val/Asp/Asn, Asp/Asn, Arg/His/Asn, Gln/Arg and Thr/Val, respectively.

The lectin shown in SEQ ID No: 5 is a novel lectin which can be extracted from *Naematoloma sublateritium* (NSL). Xaa at positions 10 and 17 of SEQ ID No: 5 may be any amino acid residues, while they are preferably Cys. Xaa at positions 13, 14 and 16 are Asp/Thr, Ser/Ala and Gln/Lys, respectively.

The lectin shown in SEQ ID No: 6 is also a novel lectin having a molecular weight of 4,500 which can be extracted from *Naematoloma sublateritium* (NSL). SEQ ID No: 6 is a variant in which one Asn is inserted into the peptide of SEQ ID No: 5. Therefore, Xaa at positions 10 and 18 of SEQ ID No: 6 may be any amino acid residues, while they are preferably Cys. Xaa at positions 14, 15 and 17 are Asp/Thr, Ser/Ala and Gln/Lys, respectively.

The fucose α1→6 specific lectin may comprise usually 2-10, preferably 2-4 subunits of the lectin of SEQ ID Nos: 2-6 which are linked together.

TABLE 1

| Name | Amino acid sequence | SEQ ID No: |
|------|---------------------|------------|
|  | Cys Asp Gly Xaa Xaa Xaa Xaa Cys | 1 |
| PTL | Ala Pro Val Pro Val Thr Lys Leu Val Xaa Asp Gly Asp Thr Tyr Lys Xaa Thr Ala Xaa Leu Asp Xaa Gly Asp Gly Xaa Trp Val Ala Gln Trp Xaa Thr Xaa Val Phe His Xaa Gly | 2 |
| SRL | Ala Pro Val Xaa Val Thr Xaa Leu Xaa Xaa Asp Gly Xaa Ser Tyr Lys Xaa Thr Ala Xaa Leu Asp Tyr Gly Asp Gly Xaa Trp Xaa Ala Gln Trp Xaa Xaa Asn Val Phe His Xaa | 3 |
| LSL | Xaa Pro Val Xaa Val Lys Xaa Xaa Xaa Xaa Asp Gly Xaa Thr Tyr Xaa Xaa Thr Ala Xaa Leu Xaa Tyr Gly Xaa Gly Xaa Trp Val Ala Xaa Trp Ser Xaa Ala Val Phe His Gln Ser | 4 |
| NSL | Ala Pro Val Pro Val Thr Lys Leu Val Xaa Asp Gly Xaa Xaa Phe Xaa Xaa Thr Ala Asn Leu Asp Phe Gly Asp Gly Asn Trp Val Ala Gln Trp Ser Thr Asn Val Phe His Asn | 5 |
| NSL | Ala Pro Val Pro Val Thr Lys Leu Val Xaa Asp Asp Gly Xaa Xaa Phe Xaa Xaa Thr Ala Asn Leu Asp Phe Gly Asp Gly Asn Trp Val Ala Gln Trp Ser Thr Asn Val Phe His Asn | 6 |

The fucose α1→6 specific lectin may be (a) a protein or peptide comprising an amino acid sequence set forth in any of SEQ ID Nos: 2-5, as well as (b) a protein or peptide having one or more amino acids deleted, inserted or replaced in the amino acid sequence shown in any of SEQ ID Nos: 2-5, and in addition, functionally equivalent to a protein or peptide comprising an amino acid sequence shown in any of SEQ ID Nos: 2-5. Wherein "functionally equivalent" means that the protein or peptide has affinity for a fucose α1→6 sugar chain with a binding constant of $1.0 \times 10^4$ $M^{-1}$ or more, preferably $1.0 \times 10^5$ $M^{-1}$ or more, and more preferably $1.0 \times 10^6$ $M^{-1}$ or more. An example of a variant in (b) is the protein or peptide shown in SEQ ID No: 6.

The fucose α1→6 specific lectin is in particular preferably PTL, SRL, NSL, LSL and *Amanita muscaria* lectin (AML), and more preferably PTL and SRL. PTL and SRL, are most suitable for a fucose α1→6 specific lectin used in the discrimination method of the present invention because they bind to neither any fucose other than a fucose α1→6, nor high mannose sugar chains having no fucose, showing different properties from the conventional fucose α1→6 affinity lections.

The fucose α1→6 specific lectin can be isolated from basidiomycetes using known extraction, separation, or purification methods, etc or proper combination thereof. For example, they include a step of obtaining an aqueous medium extract from basidiomycetes using an aqueous medium as an extracting solvent. From the extract, a lectin can be obtained, the lectin having a molecular weight of 4,000 to 40,000, preferably 4,000-20,000 as measured by the SDS polyacrylamide gel electrophoresis, and having affinity for fucose α1→6 sugar chains with a binding constant of $1.0 \times 10^4 \, M^{-1}$ or more, preferably $1.0 \times 10^5 \, M^{-1}$ or more, and more preferably $1.0 \times 10^6 \, M^{-1}$ or more at 25° C.

Preferably the basidiomycete is selected from at least one of the Strophariaceae, Tricholomataceae, Polyporaceae and Amanitaceae family. In particular preferably, it belongs to Strophariaceaes such as *Pholiota terrestris* Overholts, *Pholiota squarrosa* (*Pholiota squarrosa* (Fr.) Kummer), *Pholiota adiposa* (*Pholiota adiposa* (Fr.) Kummer), *Nameko mushroom* (*Pholiota nameko* (T. Ito) S.Ito & Imai), *Stropharia rugosoannulata* (*Stropharia rugosoannulata* Farlow in Murr.), *Naematoloma sublateritium* (*Naematoloma sublateritium* (Fr.) Karst or *Hypholoma sublateritium* (Fr.) Quel), Tricholomataceae such as *Lepista sordida* (*Lepista sordida* (Schum.:Fr.) Sing.), Polyporaceaes such as *Trichaptum elongatum* and *Microporus vernicipes*, and Amanitaceae such as *Amanita muscaria*. A portion of these basidiomycetes to be used is preferably fruiting body.

There is no particular limitation for a method of obtaining a water-soluble extract from an aqueous medium and fruiting body of basidiomycete as long as the aqueous medium can be allowed to have a contact with fruiting body of basidiomycete. In view of extraction efficiency, preferred is a method of fracturing fruiting body of basidiomycete in an aqueous medium into a suspension. Moreover, fracturing methods include conventional methods using a mixer, a homogenizer and the like.

The aqueous solvent may include a buffer, and a mixture of a water-miscible organic solvent and water or a buffer. Preferably, it is a buffer, or a mixture of a buffer and an organic solvent.

Any known buffer can be used as the buffer without any particular limitation. Among these, buffer solutions having buffering capacity between pH 3 and 10, more preferably between pH 6 and 8. Specifically, they include phosphate buffer, citrate buffer, acetic acid buffer, and Tris buffer. In particular, phosphate buffer is preferred in view of extraction efficiency.

Salt concentrations in the buffer solutions are, without any particular limitation, preferably 1-100 mM, and more preferably 5-20 mM in view of extraction efficiency and buffering capacity.

The buffer solutions may further contain salts. For example, phosphate-buffered saline where sodium chloride is further added to phosphate buffer, etc. is preferred as aqueous medium.

Any water-miscible organic solvents can be used as the organic solvent without any particular limitation. In particular, acetone, methanol, ethanol, 2-propanol and acetonitrile are preferred. In the case of mixing an organic solvent and water or a buffer, the organic solvent content is preferably 10 to 40% by mass.

Preferably, the extraction step further comprises a step of removing insoluble materials from a mixture of an aqueous medium and fruiting body of basidiomycete. The methods of removing insoluble materials may include a method such as filtration and centrifugation, but centrifugation is preferred in view of removing efficiency.

In particular, the extraction step is preferably a step of fracturing fruiting body of basidiomycete in phosphate-buffered saline and removing insoluble materials by centrifugation to obtain an aqueous medium extract.

For a method of manufacturing the fucose α1→6 specific lectin, the use of any of the following purification methods allows more efficient purification.

Purification Method 1

The aqueous medium extract obtained by the above step is subjected to ammonium sulfate precipitation to obtain a lectin containing fraction, which is then purified by hydrophobic chromatography and reversed phase chromatography.

Purification Method 2

The aqueous medium extract obtained by the above step is subjected to affinity chromatography using the supports in which thyroglobulin is immobilized to agarose and the like.

Purification Method 3

The water-soluble extract obtained by the above step is subjected to ammonium sulfate precipitation to obtain a lectin containing fraction, which is then dialyzed and lyophilized. The crude lectin fraction is then dissolved in Tris buffer and subsequently subjected to ion exchange chromatography. The resulting active fraction is then concentrated and subsequently separated using gel filtration chromatography.

The method of manufacturing the fucose α1→6 specific lectin may comprise a step of dialyzing the lectin containing fraction obtained in the above purification step, and a step of lyophilizing the dialyzed lection solution. Thereby, the lectin can be easily isolated. The dialysis step and the lyophilization step can be performed by commonly-used known methods.

The fucose α1→6 specific lectin, which is (a) a protein or peptide comprising the amino acid sequence set forth in any of SEQ ID Nos: 2-5, or (b) a protein or peptide having one or more amino acids deleted, inserted or replaced in the amino acid sequence shown in any of SEQ ID Nos: 2-5, and in addition, functionally equivalent to a protein or peptide comprising the amino acid sequence shown in any of SEQ ID Nos: 2-5, may be extracted from natural plant as well as may be artificially expressed in a non-native host or chemically synthesized. Expression in a host and chemical synthesis can be performed by commonly-used known methods.

Preferably a labeling means is pre-incorporated into the fucose α1→6 specific lectin used for detection. Such a lectin may be hereafter referred to as a labeled lectin. A labeled lectin comprises at least a fucose α1→6 specific lectin and a labeling means, and is detectably labeled.

For the above labeling means, any known labeling methods can be applied without any particular limitation, including, for example, labeling with a radioactive isotope and attaching a labeled compound.

For the above labeled compounds, any compounds commonly used for this purpose can be applied without any particular limitation, including, for example, a directly or indirectly labeled compound, an enzyme, and a fluorescence compound. Specifically, they may include biotin, digoxigenin, horseradish derived peroxidase, fluorescein isothiocyanate and CyDye. These labeled compounds can be conventionally attached to a lectin.

There is no particular limitation for the above samples as long as they are obtained from a living body comprised of animal including human, the samples including, for example, blood, plasma, serum, tear, saliva, body fluid, milk, urine, cell culture supernatants, secreted materials from a transgenic animal. When the detection method of the present invention is used for pancreatic cancer screening, serum or plasma taken from human can be used as a sample. Serum can be conventionally extracted from blood.

The fucose α1→6 specific lectins will show high affinity for any sugar chains having a fucose α1→6 linkage (for example, Immunoglobulin G, α-fetoprotein, prostate-specific antigen, etc. shown in Table 1). In order to eliminate the detection of these sugar chains, the method of the present invention preferably detects pathological haptoglobin by a sandwich assay using the fucose α1→6 specific lectin and anti-haptoglobin antibody.

For the sandwich assay, first of all, the anti-haptoglobin antibody is allowed to react with a sample such as cell culture supernatant and serum to obtain a complex of haptoglobin or pathological haptoglobin with the anti-haptoglobin antibody. These complexes are isolated and purified by affinity chromatography, immunoprecipitation, etc. Then, the complex is allowed to react on the fucose α1→6 specific lectin to obtain a lectin-pathological haptoglobin-anti-haptoglobin antibody complex.

Alternatively, in the sandwich assay, the fucose α1→6 specific lectin may be first allowed to react with a sample containing pathological haptoglobin to obtain a lectin-pathological haptoglobin complex, and then the lectin-pathological haptoglobin complex may be allowed to react with the anti-haptoglobin antibody to obtain a lectin-pathological haptoglobin-anti-haptoglobin antibody complex.

Anti-haptoglobin antibody which can specifically recognize haptoglobin can be obtained based on the conventional methods. One example is a method of immunizing animal with haptoglobin as an antigen to obtain anti-haptoglobin antibody. Anti-haptoglobin antibody may be either a polyclonal antibody or a monoclonal antibody.

The methods for the detection of binding of the fucose α1→6 specific lectin with pathological haptoglobin include ELISA (sandwich ELISA, etc.), lectin chromatography, lectin blotting, lectin staining, a lectin chip, the condensation method and the surface plasmon resonance method such as Biacore® system. In particular, the detection method using avidin-biotin or streptavidin-biotin system is preferred due to their high sensitivity.

In the sandwich ELISA, anti-haptoglobin antibody is added and immobilized to a plate before adding samples such as serum. Then, a biotin-labeled fucose α1→6 specific lectin is added, allowing the fucose α1→6 specific lectin to react with pathological haptoglobin contained in serum. A HRP (horseradish peroxidase) labeled streptavidin solution is added as a secondary labeled compound, allowing the biotin to react with the streptavidin. Next, the HRP chromogenic substrate is added to measure the intensity of color with an absorptiometer (for HRP, a wavelength of 450 nm). If a calibration curve is created in advance using a standard sample containing a known concentration of pathological haptoglobin, quantifying pathological haptoglobin is also possible.

Lectin chromatography is affinity chromatography which uses the property of carrier-immobilized lectin to specifically bind with a sugar chain. High throughput may be expected when combined with HPLC.

Gel materials such as agarose, dextran, cellulose, starch and polyacrylamide are generally used as a carrier on which the fucose α1→6 specific lectin is immobilized. Commercially available products, without any particular limitation, can be used for this purpose, including Sepharose 4B and Sepharose 6B (both from GE healthcare bioscience). Lectin chromatography columns include those in which lectin is immobilized on a micro plate or a nanowell.

The concentration of the fucose α1→6 specific lectin to be immobilized is usually 0.001 to 100 mg/mL, preferably 0.01 to 20 mg/mL. When the carrier is agarose gel, it is activated by CNBr, etc., and then lectin is coupled to it. Lectin may be immobilized in the gel having an activated spacer introduced. Moreover, after immobilizing lectin in the gel having a formyl group introduced, the gel may be reduced with $NaCNBH_3$. Moreover, a commercially available activated gel such as NHS-Sepharose (GE healthcare bioscience) may be used.

A sample of fucose α1→6 sugar chains is loaded onto a column, which is then run with a buffer solution for washing. One exemplary buffer solution is a buffer solution having a molar concentration of 5 to 500 mM, preferably 10 to 500 mM, and a pH value of 4.0 to 10.0, preferably 6.0 to 9.0, and a NaCl content of 0 to 0.5 M, preferably 0.1 to 0.2 M, and a $CaCl_2$, $MgCl_2$ or $MnCl_2$ content of 0 to 10 mM, preferably 0 to 5 mM.

Elution of fucose α1→6 sugar chains after washing the affinity column is performed in a neutral non-denaturing buffer using an elution agent such as sodium chloride, hapten sugar and the like. This buffer may be the same as above. The concentration of the elution agent is preferably a concentration of 1 to 500 mM, in particular preferably 10 to 200 mM.

The present invention also provides a method of distinguishing pancreatic cancer from pancreatitis, wherein a fucose α1→6 specific lectin is allowed to act on pathological haptoglobin contained in a sample obtained from a living body having 30 U/mL or more of CA 19-9 in serum, the lectin:
(1) being extracted from basidiomycetes,
(2) having a molecular weight of 4,000 to 40,000 as determined by the SDS polyacrylamide gel electrophoresis, and
(3) having affinity for fucose α1→6 sugar chains with a binding constant of $1.0 \times 10^4$ $M^{-1}$ or more at 25° C.

Figure 8:
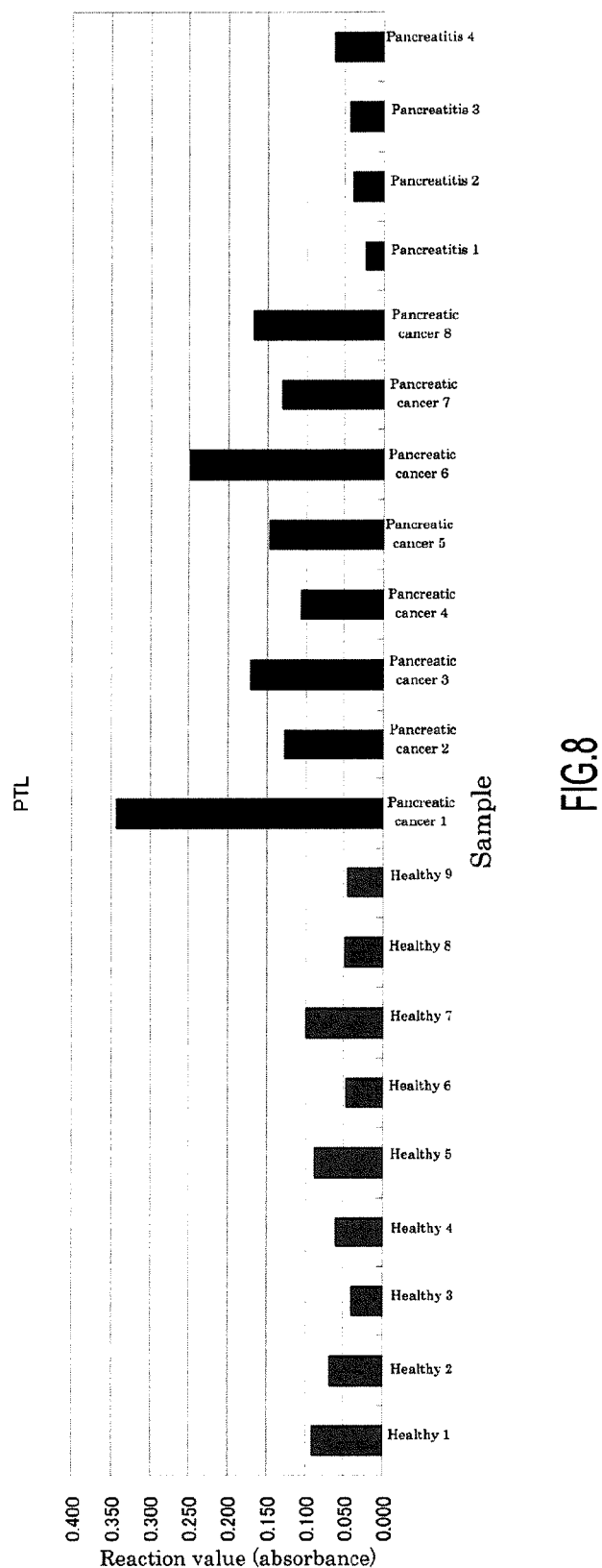
FIG. 8 shows the reaction values (absorbance) from the binding studies of haptoglobin from serum of healthy subjects and haptoglobin from serum of pancreatic cancer patients with PTL according to the present invention.

Operation of this distinction method is the same as that of the above detection method of pancreatic cancer except using a sample obtained from a living body having 30 U/mL or more of CA 19-9 in serum. As shown in Table 3 and FIG. 10, pancreatic cancer and pancreatitis are difficult to distinguish by using the conventional tumor marker CA 19-9 alone. On the other hand, according to the method of the present invention in which the marker CA 19-9 and a fucose α1→6 specific lectin are used in combination, pancreatic cancer and pancreatitis are easily distinguished as shown in FIG. 8.

The present invention also provides a diagnostic reagent or kit for detecting pancreatic cancer and/or pancreatitis, comprising a fucose α1→6 specific lectin, the lectin:
(1) being extracted from basidiomycetes,
(2) having a molecular weight of 4,000 to 40,000 as determined by the SDS polyacrylamide gel electrophoresis, and
(3) having affinity for fucose α1→6 sugar chains with a binding constant of $1.0 \times 10^4$ $M^{-1}$ or more at 25° C.

The above lectin is preferably labeled. The above diagnostic reagent or kit optionally comprises those included in known diagnostic reagent kits, such as a label (enzyme and chromogenic substrates thereof, a radioactive isotope, a luminescent material, a fluorescent material, a colored material), a buffer, a plate and a quenching solution. In particular, it preferably comprises a reagent to extract haptoglobin from a sample obtained from a living body (for example, anti-haptoglobin antibody).

EXAMPLES

The Examples of the present invention are shown below to illustrate the present invention in detail. However, the present invention is not intended to be limited to the following Examples.

Example of Preparation 1

Manufacturing PTL

According to the purification step shown below, the *Pholiota terrestris* Overholts lectin (PTL) was isolated and purified from *Pholiota terrestris* Overholts.

Extraction

The lyophilized powder (2.5 g) obtained by lyophilizing of *Pholiota terrestris* Overholts (7.5 g) was extracted with 50 ml of 10 mM Tris buffer (pH 7.2) at 4° C. for 2 hours. The resultant extract was centrifuged (15,000 rpm, 20 min, 4° C.). Then, the supernatant was subjected to gauze filtration to thereby obtain the first extract. This extraction residue was re-extracted with 50 ml of 10 mM Tris buffer (pH 7.2) at 4° C. overnight. After this extract was centrifuged (15,000 rpm, 20 min, 4° C.), the supernatant was subjected to a gauze filtration to thereby obtain the second extract. Then, these extracts were collectively filtered by a filter paper to thereby obtain *Pholiota terrestris* extract.

Ion Exchange Chromatography

Figure 4:
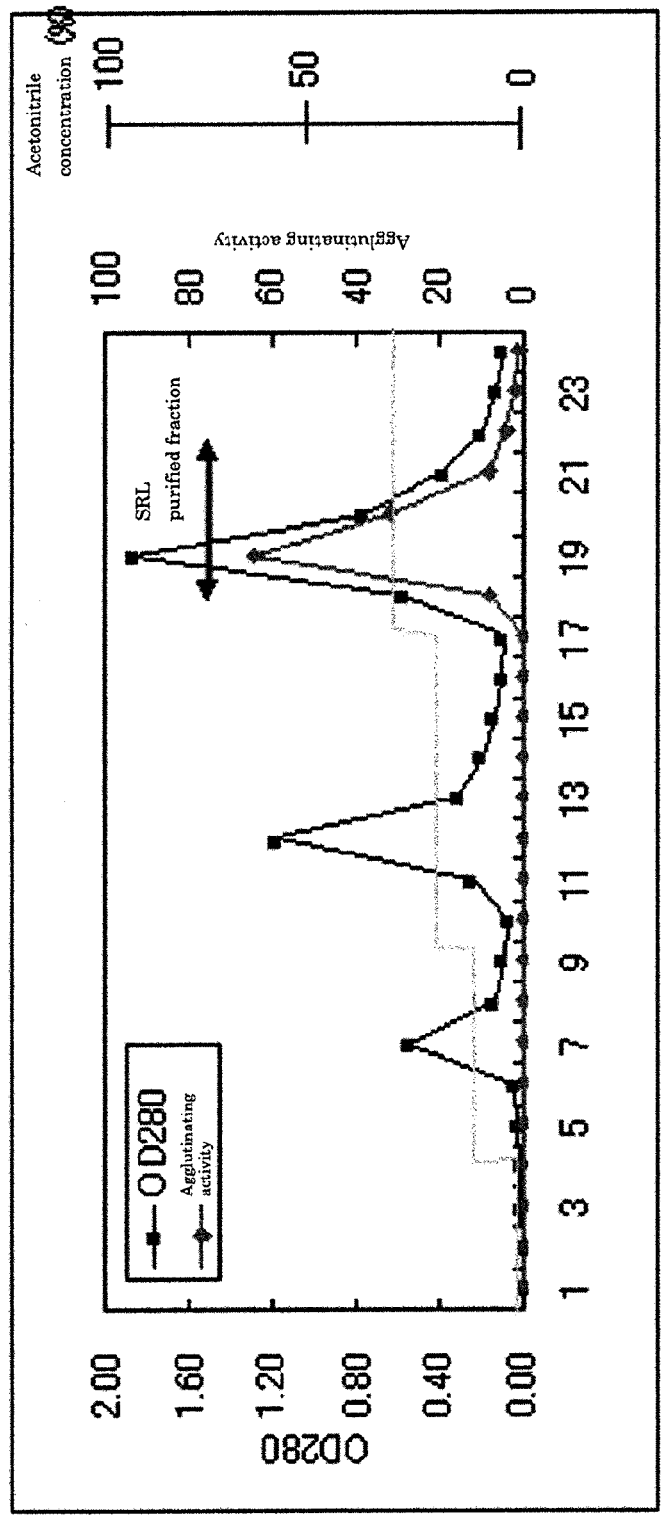
FIG. 4 shows an elution profile of reverse-phase chromatography for SRL in Example of Preparation 2.

The extract (87 ml) was applied to a column of DEAE-sepharose (GE Healthcare Bioscience) equilibrated with 10 mM Tris buffer (pH 7.2). After the column was washed with the buffer, the bound fraction was desorbed with 0.1 M NaCl in the buffer. Then, the fractions showing hemagglutination activity (shown by ←—→ of FIG. 4) were dialyzed extensively against distilled water and lyophilized.

Affinity Chromatography

Figure 2:
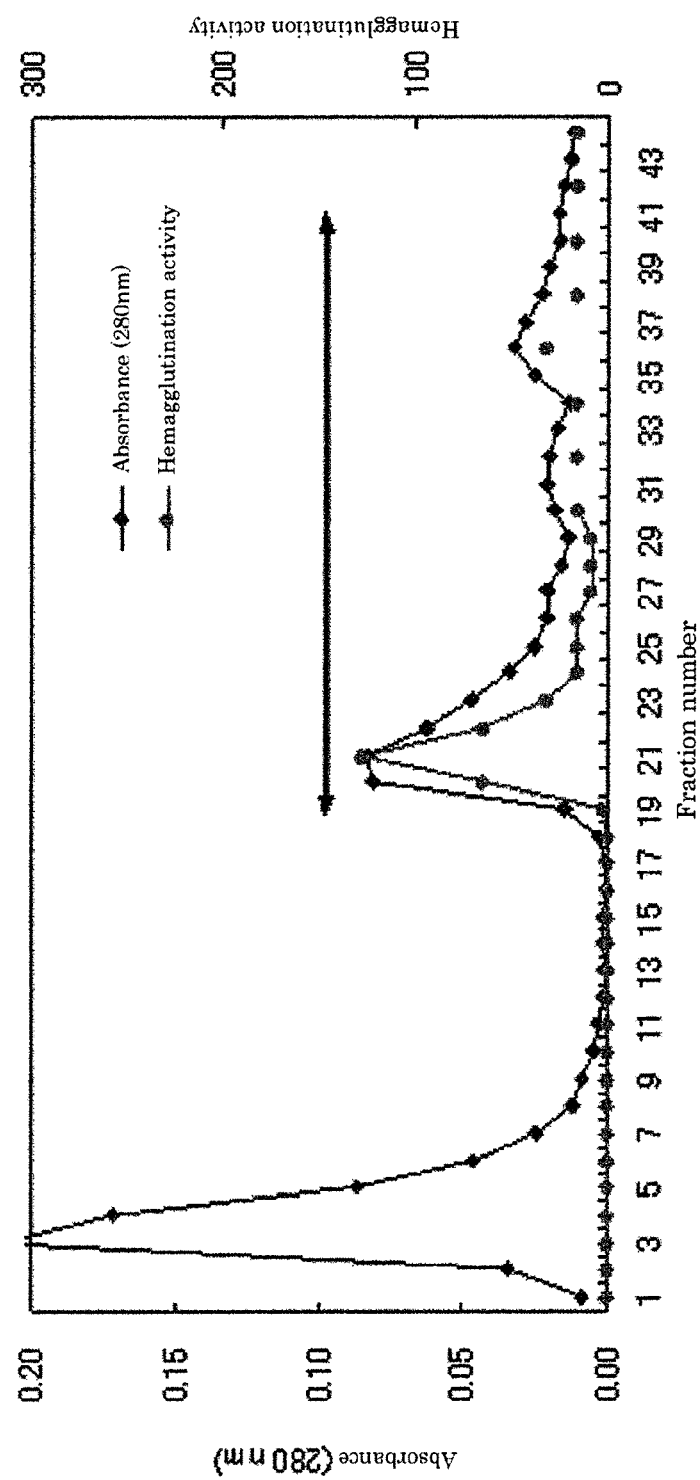
FIG. 2 shows an elution profile of affinity chromatography for PTL in Example of Preparation 1.

The lyophilized dialyzate was redissolved 10 mM phosphate buffered saline (pH 7.4, hereinafter simply referred to as PBS). Then, the extract solution was applied to a column of thyroglobulin immobilized-agarose equilibrated with the same buffer. After the column was washed with PBS, the bound fraction was desorbed with 0.2 M ammonia. Then, the fractions showing hemagglutination activity (shown by ←—→ of FIG. 2) were collected, ultrafiltered, and lyophilized, thereby obtaining 1.07 mg of PTL. The physical and chemical properties of PLT with regard to (2) molecular weight, (3) binding constants, (4) carbohydrate-binding specificity, (5) binding to branched chains and (6) amino acid sequences are described in PCT/JP2009/003346 above.

Example of Preparation 2

Manufacturing SRL

According to the purification steps shown below, *Stropharia rugosoannulata* lectin (SRL) was isolated and purified from *Stropharia rugosoannulata*.

Extraction

*Stropharia rugosoannulata* freeze-dried powders (400 g) were extracted with 1.6 L of PBS at 4° C. for 2 hours. The resultant liquid was centrifuged (15,000 rpm, 20 min, 4° C.). Then, the supernatant was subjected to a gauze filtration to thereby obtain the first extract. This extraction residue was re-extracted with 0.8 L of PBS at 4° C. overnight. This extract was centrifuged (10,000 rpm, 20 min, 4° C.). Then, the supernatant was subjected to a gauze filtration to thereby obtain the second extract. These extracts were mixed to thereby obtain *Stropharia rugosoannulata* extraction liquid.

Ammonium Sulfate Precipitation

Solid $(NH_4)_2SO_4$ (1.3 kg) was added to the resulting supernatant (2.4 L) to obtain 80% saturation. After standing at 4° C. overnight, the precipitates were collected by centrifugation (10,000 rpm, 20 min, 4° C.) and dialyzed extensively against distilled water and lyophilized, thereby collecting *Stropharia rugosoannulata*-80% ammonium sulfate precipitation fraction.

Hydrophobic Chromatography

Figure 3:
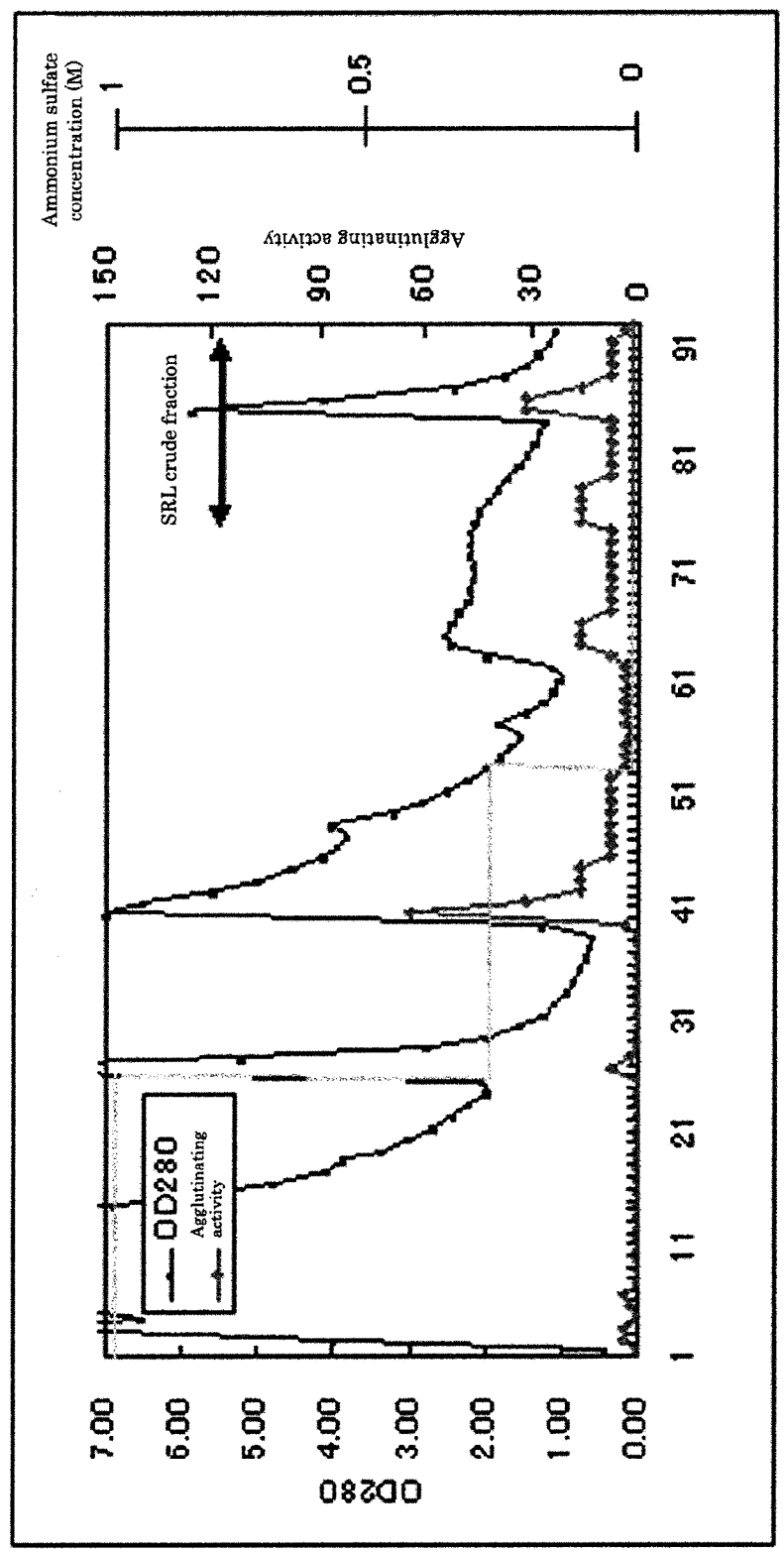
FIG. 3 shows an elution profile of hydrophobic chromatography for SRL in Example of Preparation 2.

The *Stropharia rugosoannulata*-80% ammonium sulfate precipitation fraction was applied to Butyl-TOYOPEARL 650M (TOSOH CORPORATION) equilibrated with 2 M of ammonium sulfate-PBS to perform hydrophobic chromatography purification. In this chromatography, distilled water elution fractions were collected, ultrafiltered, and lyophilized, thereby obtaining the *Stropharia rugosoannulata* lectin crude fraction (shown by ←—→ of FIG. 3).

Reversed-Phase Chromatography

The *Stropharia rugosoannulata* lectin crude fraction was applied to the C8 column (Wako Pure Chemical Industries, Ltd.) equilibrated with 0.05% trifluoroacetic acid (TFA)/acetonitrile (100/0). In this chromatography, 0.05% TFA/acetonitrile (70/30) elution fraction (shown by ←—→ of FIG. 4) was collected. Then, solvent was removed by evaporation at a room-temperature and the resultant dry powders were collected, thereby obtaining 7.5 mg of SRL. The physical and chemical properties of SRL with regard to (2) molecular weight, (3) binding constants, (4) carbohydrate-binding specificity, (5) binding to branched chains and (6) amino acid sequences are described in PCT/JP2009/003346 above.

Reference Example 1

Detection of Various Glycoproteins in Serum by the Lectins

Affinity between the glycoproteins shown in Table 1 and the biotin labeled lectins shown below was investigated by ELISA: PTL (a fucose α1→6 specific lectin which can be used in the present invention), and The following commercially available lectins which are thought to be fucose specific: LCA (Seikagaku Biobusiness Corporation, J-OIL MILLS, Inc), AAL (Seikagaku Biobusiness Corporation, J-OIL MILLS, Inc), *Lotus* (Seikagaku Biobusiness Corporation, J-OIL MILLS, Inc), and UEA-I (Seikagaku Biobusiness Corporation, J-OIL MILLS, Inc).

Serum glycoprotein (human serum albumin (CALBIOCHEM), Immunoglobulin G (Sigma), transferrin (Sigma), fibrinogen (AbD Serotec), Immunoglobulin A (BETYL) α2-macroglobulin (BMO), Immunoglobulin M (ROCKLAND), Complement C3 (CALBIOCHEM), haptoglobin (BIODESIGN), α1-acidic glycoprotein (Sigma), α-fetoprotein (Fitzgerald), α-fetoprotein L3 (Wako Pure Chemical Industries, Ltd) and prostate-specific antigen (Scipac) were dissolved in PBS at 1 mg/mL, and further diluted to 10 ng/mL with 0.1 M carbonate buffer (pH 9.5). Fifty μL of the diluted solution was added to a microtiter plate (Nunc 439454), and then incubated at 37° C. for 1 hour. After washed once with 0.05% Tween 20 (polyoxyethylene sorbitan monolaurate) (hereafter abbreviated as Tween)/PBS, 200 μL of 1% bovine serum albumin (BSA)/PBS was added to the wells, and then incubated at 37° C. for 1 hour. The plate was washed twice with 0.05% Tween/PBS.

Fifty μL of the biotin labeled lectin solution prepared to 1 μg/mL with 1% BSA/0.05% Tween/PBS was added to the wells, and then left at room temperature for 1 hour. After washed twice with 0.05% Tween/PBS, 50 μL of the HRP labeled streptavidin solution (1 μg/mL) diluted with 1% BSA/0.05% Tween/PBS was added to the wells, and then left at room temperature for 30 minutes. After washed three times with 0.05% Tween/PBS, 50 μL of the HRP chromogenic substrate (product name: TMB Peroxidase substrate system, KPL) was added, and then left at room temperature for 5 minutes.

To quench the reaction, 50 μL of 1M phosphate was added. The absorbance at 450 nm was measured in the POWER-SCAN® HT plate reader (DS PHARMA).

The absorbance values at 450 nm were subtracted by the absorbance value from the well on the plate in which no glycoprotein was immobilized, and the resulting values were taken as reaction values. Affinity was ranked by classifying the reaction values according to the following criteria. The results are shown in Table 2.
High: 0.5 or more,
Moderate: 0.2 to 0.5,
Low: 0.1 to 0.2,
Not bound: 0 to 0.1.

evaluated by ELISA, respectively. Similar tests as PTL were also performed for LCA and AAL as a positive control.

Extraction of Haptoglobin from Pancreatic Cancer Cells

Thousand mL of the culture supernatant of the pancreatic cancer cell line was concentrated to 1 mL with an ultrafiltration filter (Product name: VIVA SPIN 20-10 K, SARTORIUS). The above concentrated solution was added to the gel

TABLE 2

| | | Lectin species | | | | |
|---|---|---|---|---|---|---|
| Protein | Carbohydrate information | *Pholiota terrestris* Overholts lectin PTL | *Lens culinaris* lectin LCA | *Aleuria aurantia* lectin AAL | *Lotus japonicuslectin* Lotus | *Ulex europaeus* lectin UEA-1 |
| Human serum albumin (HAS) | No sugar chain | Not bound | Not bound | Low | Not bound | Not bound |
| Immunoglobulin G (IgG) | N-linked glycan having α1→6 fucose | Low | Not bound | Low | Not bound | Not bound |
| Transferrin (TF) | N-linked glycan not including α1→6 L-fucose | Not bound | Not bound | Low | Not bound | Not bound |
| Fibrinogen (FB) | N-linked glycan not including α1→6 L-fucose | Not bound | Not bound | Low | Not bound | Not bound |
| Immunoglobulin A (IgA) | N-linked glycan having α1→6 fucose | Moderate | Not bound | Moderate | Not bound | Not bound |
| α2-Macroglobulin (α2MG) | N-linked glycan having α1→6 fucose | Moderate | Not bound | High | Not bound | Not bound |
| Immunoglobulin M (IgM) | N-linked glycan having α1→6 fucose | Low | Not bound | Moderate | Not bound | Not bound |
| Complement C3 (C3) | Having sugar chains, but details unknown | Not bound | Not bound | Low | Not bound | Not bound |
| Haptoglobin (HP) | N-linked and O-linked glycans containing almost no fucose | Not bound | Not bound | Low | Not bound | Not bound |
| α1-Acid glycoprotein (AGP) | N-linked glycan not including α1→6 L-fucose | Not bound | Not bound | Moderate | Not bound | Not bound |
| α-Fetoprotein (AFP) | N-linked glycan containing no fucose | Not bound | Not bound | Moderate | Not bound | Not bound |
| α-Fetoprotein (AFP-L3) | N-linked glycan having α1→6 fucose | High | High | High | Not bound | Not bound |
| Prostate-specific antigen (PSA) | Sugar chain containing fucose | High | Not bound | Moderate | Not bound | Not bound |

PTL had affinity for α-fetoprotein L3 (AFP-L3) and prostate-specific antigen (PSA) containing fucose α1→6, while it did not show affinity for haptoglobin essentially having no fucose. LCA shows affinity only for AFP-L3. AAL shows affinity for many fucosylated proteins, such as IgA and α2MG. It has a binding mode similar to that of PTL, while it often shows significant nonspecific absorption. Lotus and UEA-I have low affinity for glycoproteins in serum.

Taken these results together, LCA, Lotus and UEA-I previously known to have affinity for fucose also may not be able to detect glycoproteins having a fucose α1→6 sugar chain. Moreover, AAL also detects glycoproteins other than the ones having a fucose α1→6 sugar chain. On the other hand, PTL has affinity only for glycoproteins having a fucose α1→6 sugar chain.

Example 1

Detection of Pathological Haptoglobin in the Culture Supernatant of a Pancreatic Cancer Cell Line by ELISA Using PTL Reference Example 1 revealed that PTL did not have affinity for haptoglobin. Therefore, the ability of PTL to detect haptoglobin extracted from the culture supernatant of a pancreatic cancer cell line (PSN-1, available from DS PHARMA) and haptoglobin extracted from human serum (available from BIODESIGN) as a negative control was (NHS-activated Sepharose 4 Fast Flow (GE healthcare) in which anti-haptoglobin antibody (The Binding Site) was pre-immobilized. One hour after mixing it every 10 minutes at room temperature, the solution containing the gel was added to a 0.45 μm filter tube (Millipore), then centrifugation was performed at 400×g at the temperature of 4° C. for 5 minutes, and then the filtrate was discarded. Next, 200 μL of PBS was added, and then centrifugation was performed at 400×g at the temperature of 4° C. for 5 minutes, and then the filtrate was discarded. This was repeated twice. Next, 200 μL of Elution Buffer (100 mM glycine, 0.5M NaCl, pH 3.0) was added, and then centrifugation was performed at 400×g at the temperature of 4° C. for 5 minutes, and the filtrate was collected. This was repeated twice. After neutralizing the haptoglobin (HP) solution obtained by combining these solutions by 3N NaOH, 600 μL of PBS was added.

Quantification of Haptoglobin by ELISA

The amount of haptoglobin contained in the HP solution was quantified by ELISA as follows. Haptoglobin from human serum (BIODESIGN) was dissolved in 1% BSA/PBS at 0 to 200 ng/mL, which were used as standard haptoglobin solutions. Mouse monoclonal anti-haptoglobin antibody (Nippon Biotest Laboratories inc.) was diluted 10,000 times with 0.1 M carbonate buffer (pH 9.5). Fifty μL of the diluted solution was added to a microtiter plate(Nunc), and incubated at 37° C. for 1 hour. After washed once with 0.05% Tween/PBS, 200 μL of 1% BSA/PBS was added to the wells, and incubated at 37° C. for 1 hour. After washed twice with 0.05%

Tween/PBS, 50 μL of the standard haptoglobin solution, or the HP solution was added, and incubated at 37° C. for 1 hour. After washed twice with 0.05% Tween/PBS, 50 μL of a sheep polyclonal anti-haptoglobin antibody (The Binding Site) solution suitably diluted with 1% BSA/0.05% Tween/PBS was added to the wells, and left at room temperature for 1 hour. After washed twice with 0.05% Tween/PBS, 50 μL of a HRP labeled anti-sheep IgG antibody (Millipore) solution suitably diluted with 1% BSA/0.05% Tween/PBS was added, and left at room temperature for 30 minutes. After washed three times with 0.05% Tween/PBS, 50 μL of the HRP chromogenic substrate (Product name: TMB Peroxidase substrate system, KPL) was added, and left at room temperature for 5 minutes. To quench the reaction, 50 μL of 1 M phosphate was added. The absorbance at 450 nm was measured in a plate reader (Product name: POWERSCAN® HT, DS PHARMA).

A calibration curve was created from the absorbance of standard haptoglobin solutions, from which the concentration of haptoglobin in the HP solution derived from pancreatic cancer cells was calculated.

Reaction of PTL with Pathological Haptoglobin

Pathological haptoglobin contained in the HP solution was detected by ELISA as follows. The HP solution obtained above was diluted with 0.1 M carbonate buffer (pH 9.5) such that haptoglobin was 10 ng/mL (the HP diluted solution). Similarly, Haptoglobin from human serum (BIODESIGN) was also prepared to 10 ng/mL as a negative control (the human serum-derived haptoglobin solution). To a microtiter plate (Nunc), 50 μL of the HP diluted solution and the human serum-derived haptoglobin solution was added, and incubated at 37° C. for 1 hour. After washed once with 0.05% Tween/PBS, 200 μL of 1% BSA/PBS was added to the wells, and incubated at 37° C. for 1 hour.

After washed twice with 0.05% Tween/PBS, 50 μL of the biotin-labeled PTL solution suitably diluted with 1% BSA/0.05% Tween/PBS was added to the wells, and left at room temperature for 1 hour. After washed twice with 0.05% Tween/PBS, 50 μL of the HRP labeled streptavidin solution (1 μg/mL) diluted with 1% BSA/0.05% Tween/PBS was added to the wells, and left at room temperature for 30 minutes. After washed three times with 0.05% Tween/PBS, 50 μL of the HRP chromogenic substrate (Product name: TMB Peroxidase substrate system, KPL) was added, and left at room temperature for 5 minutes. To quench the reaction, 50 μL of 1M phosphate was added. The absorbance at 450 nm was measured in a plate reader (Product name: POWERSCAN® HT, DS PHARMA).

For comparison, similar tests in which LCA and AAL were used instead of PTL were also conducted.

The absorbance values at 450 nm were subtracted by the absorbance value from the well on the plate in which no glycoprotein was immobilized, and the resulting values were taken as reaction values. The reaction values of haptoglobin from human serum and pancreatic cancer cells are shown in FIGS. 5-7.

Figure 5:
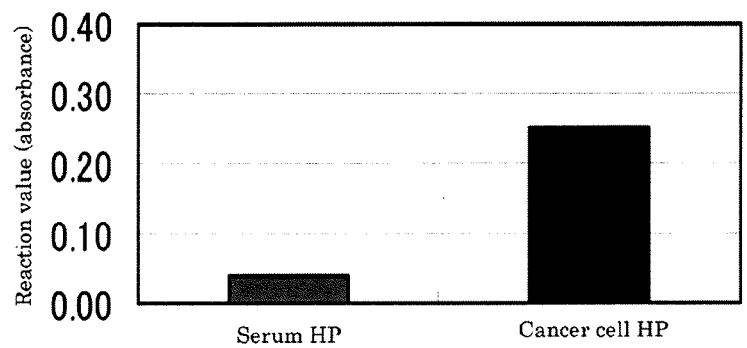
FIG. 5 shows reaction values (absorbance) when haptoglobins from human serum (Serum HP) and from the supernatant of pancreatic cancer cells (Cancer cell HP) were respectively allowed to bind to PTL according to the present invention.
Figure 6:
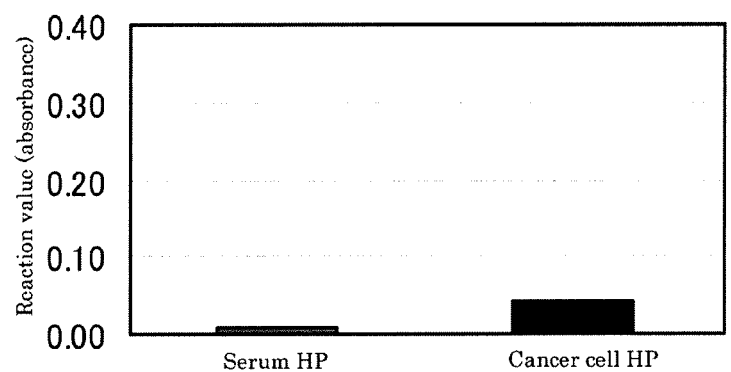
FIG. 6 shows reaction values when Serum HP and Cancer cell HP were respectively allowed to bind to LCA of the comparative example as in FIG. 5.
Figure 7:
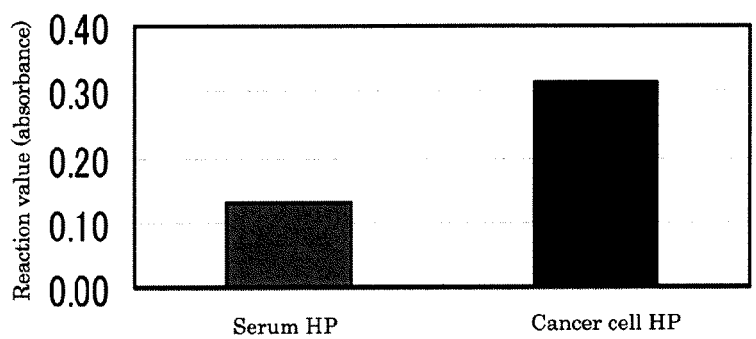
FIG. 7 shows reaction values when Serum HP and Cancer cell HP were respectively allowed to bind to AAL of the comparative example as in FIG. 5.

As shown in FIGS. 5-7, PTL does not have affinity for haptoglobin from human serum. However, it has affinity for haptoglobin from the culture supernatant of pancreatic cancer cells. For LCA, the affinity is low for both haptoglobin from pancreatic cancer cells and from human serum. AAL also can detect the difference between them, although their relative ratio is smaller than that of PTL. From the results above, it is clear that pancreatic cancer can be detected by allowing PTL, a fucose α1→6 specific lectin, to act on haptoglobin from pancreatic cancer cells. Example 2: Detection of pathological haptoglobin in serum from pancreatic cancer patients by ELISA using PTL Example 2

Detection of Pathological Haptoglobin in the Serum of Pancreatic Cancer Patient by ELISA Using PTL According to Example 1, it is clear that pathological haptoglobin as a tumor marker of pancreatic cancer can be detected by using PTL, a fucose α1→6 specific lectin. Accordingly, the ability of PTL to detect pathological haptoglobin in serum from the following individuals was indeed evaluated by ELISA, respectively: healthy subjects (n=9, 6 males, 3 females, the mean age: 32.8) (abbreviation: healthy 1-9), pancreatic cancer patients (n=8, 4 males, 4 females, the mean age: 52.1) (abbreviation: pancreatic cancer 1-8) and pancreatitis patients (n=4, 1 male, 3 females, the mean age: 59.5) (abbreviation: pancreatitis 1-4). For comparison, similar tests as PTL were also conducted with AAL.

Extraction of Haptoglobin from Serum

Ten μL of serum samples from the healthy subjects, the pancreatic cancer patients and the pancreatitis patients were diluted with 190 μL of PBS. The diluted serum solutions were added to the anti-haptoglobin antibody (The Binding Site) immobilized gel. It was left at room temperature for 1 hour with mixing every 10 minutes. The solution containing the gel was added to a 0.45 μL filter tube (Millipore), and then centrifugation was performed at 400×g at 4° C. for 5 minutes, and the filtrate was discarded. Next, 200 μL of PBS was added, and centrifugation was then performed at 400×g at 4° C. for 5 minutes, and the filtrate was discarded. This was repeated twice. Then 200 μL of Elution Buffer (100 mM glycine, 0.5 M NaCl, pH 3.0) was added, and then centrifugation was performed at 400×g at the temperature of 4° C. for 5 minutes, and the filtrate was collected. This was repeated twice. The filtrates obtained were combined and taken as the HP solution, and neutralized with 3N NaOH, and then 600 μL of PBS was added.

Detection of Pathological Haptoglobin by ELISA

Pathological haptoglobin contained in the HP solution was detected by ELISA as follows. First, the HP solution obtained above was diluted 10 times with 0.1 M carbonate buffer (pH 9.5). Fifty μL of the diluted solution was added to a microtiter plate (Nunc), and incubated at 37° C. for 1 hour. After washed once with 0.05% Tween/PBS, 200 μL of 1% BSA/PBS was added to the wells, and incubated at 37° C. for 1 hour. After washed twice with 0.05% Tween/PBS, 50 μL of the biotin-labeled lectin solution suitably diluted with 1% BSA/0.05% Tween/PBS was added to the wells, and left at room temperature for 1 hour. After washed twice with 0.05% Tween/PBS, 50 μL of the HRP labeled streptavidin solution (1 μg/mL) diluted with 1% BSA/0.05% Tween/PBS was added to the wells, and left at room temperature for 30 minutes. After washed three times with 0.05% Tween/PBS, 50 μL of the HRP chromogenic substrate (Product name: TMB Peroxidase substrate system, KPL) was added, and left at room temperature for 5 minutes. To quench the reaction, 50 μL of 1 M phosphate was added. The absorbance at 450 nm was measured in a plate reader (Product name: POWERSCAN® HT, DS PHARMA).

The absorbance values at 450 nm were subtracted by the absorbance value from the well on the plate in which no glycoprotein was immobilized, and the resulting values were taken as reaction values. The results are shown in FIGS. 8 and 9.

Figure 9:
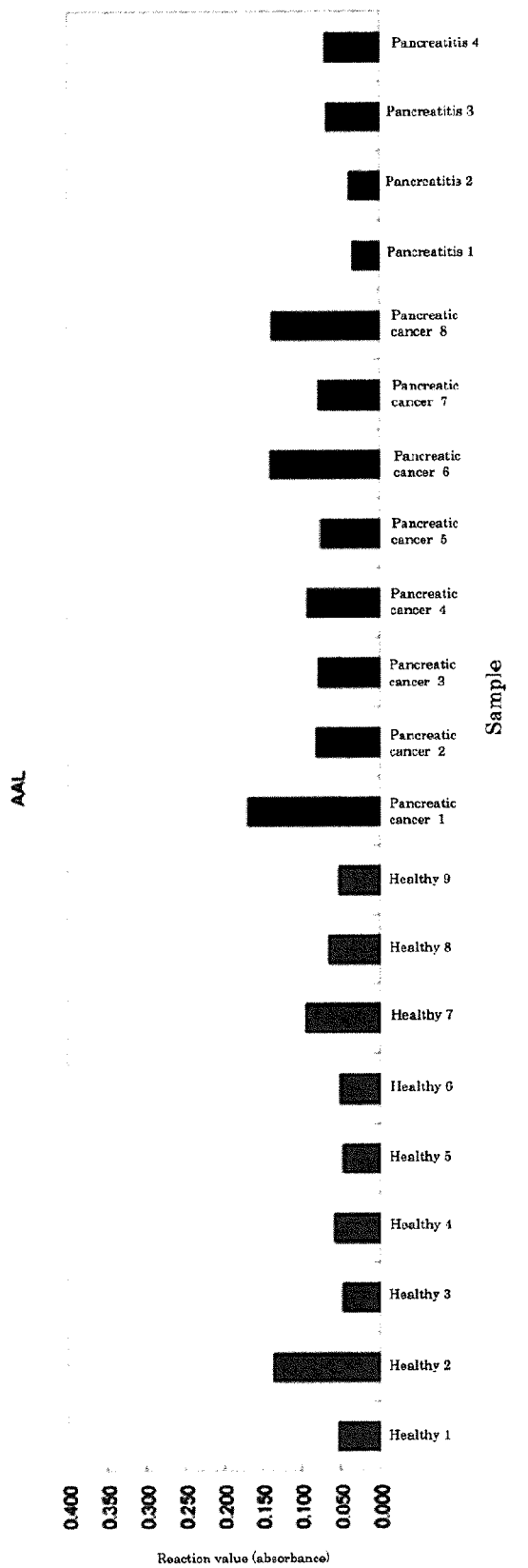
FIG. 9 shows reaction values from the binding studies in which PTL was replaced with AAL of the comparative example.

As shown in FIGS. 8 and 9, the reaction values for pathological haptoglobin by PTL show distinctively higher values only for sera from the pancreatic cancer patients than those for sera from the healthy subjects and the pancreatitis patients. AAL was able to detect the difference between the healthy subjects and the pancreatic cancer patients, while for some patients it also detected reaction values lower than those for the healthy subjects.

Quantification of CA 19-9 by ELISA

Quantification of the tumor marker CA 19-9 contained in sera from healthy subjects, pancreatic cancer patients and pancreatitis patients was performed by ELISA as follows. Lyphocheck Tumor Maker Control (BIO-RAD) was used as a standard sample. Mouse monoclonal anti-CA 19-9 antibody (Fitzgerald) was diluted 1000 times with 0.1M carbonate buffer (pH 9.5). Fifty μL of the diluted solution was added to a microtiter plate(Nunc), and incubated at 37° C. for 1 hour. After washed once with 0.05% Tween/PBS, 200 μL of 1% BSA/PBS was added to the wells, and incubated at 37° C. for 1 hour. After washed twice with 0.05% Tween/PBS, 50 μL of each serum was added, and incubated at 37° C. for 1 hour. After washed twice with 0.05% Tween/PBS, 50 μL of a rabbit polyclonal anti-CA 19-9 antibody (Acris) solution suitably diluted with 1% BSA/0.05% Tween/PBS was added to the wells, and incubated at 37° C. for 1 hour. After washed twice with 0.05% Tween/PBS, 50 μL a HRP labeled anti-rabbit IgG antibody (Nippon Chemi-Con Corporation) solution suitably diluted with 1% BSA/0.05% Tween/PBS was added, and left at 37° C. for 30 minutes. After washed three times with 0.05% Tween/PBS, 50 μL of the HRP chromogenic substrate (Product name: TMB Peroxidase substrate system, KPL) was added, and left at room temperature for 5 minutes. To quench the reaction, 50 μL of 1 M phosphate was added. The absorbance at 450 nm was measured in a plate reader (Product name: POWERSCAN® HT, DS PHARMA).

A calibration curve was created from the reaction values of the standard sample, from which the concentrations of CA 19-9 in each serum were calculated. The results are shown in Table 3 and FIG. 10.

TABLE 3

| Sample | The amount of CA 19-9 (U/mL) |
|---|---|
| Healthy 1 | 28.6 |
| Healthy 2 | 19.1 |
| Healthy 3 | 6.5 |
| Healthy 4 | 9.5 |
| Healthy 5 | 20.5 |
| Healthy 6 | 23.9 |
| Healthy 7 | 21.2 |
| Healthy 8 | 22.0 |
| Healthy 9 | 24.3 |
| Pancreatic cancer 1 | 56.3 |
| Pancreatic cancer 2 | 42.6 |
| Pancreatic cancer 3 | 46.8 |
| Pancreatic cancer 4 | 41.6 |
| Pancreatic cancer 5 | 43.5 |
| Pancreatic cancer 6 | 68.4 |
| Pancreatic cancer 7 | 45.8 |
| Pancreatic cancer 8 | 52.3 |
| Pancreatitis 1 | 35.1 |
| Pancreatitis 2 | 37.0 |
| Pancreatitis 3 | 39.0 |
| Pancreatitis 4 | 35.7 |

Figure 10:
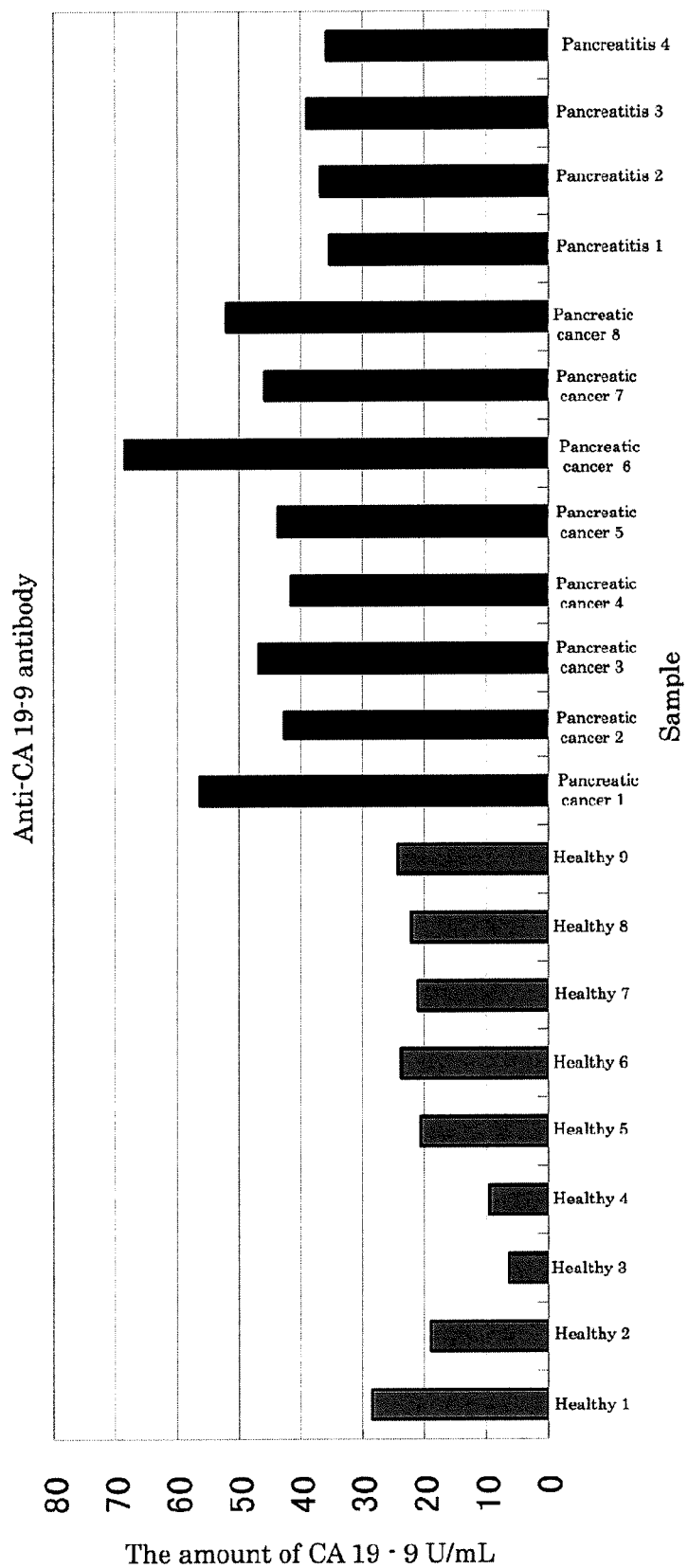
FIG. 10 shows the results of the quantification of CA 19-9 in serums of healthy subjects, pancreatic cancer patients and pancreatitis patients by a sandwiches assay using mouse monoclonal anti-CA 19-9 antibody and rabbit polyclonal anti-CA 19-9 antibody.

As shown in FIG. 10, the amount of CA 19-9 in sera from the healthy subjects, the pancreatic cancer patients and the pancreatitis patients shows distinctively higher values for both sera from the pancreatitis patients and pancreatic cancer patients than those for sera from the healthy subjects. Therefore, it is clear that distinguishing pancreatic cancer from pancreatitis is difficult by detecting CA 19-9 alone.

On the other hand, as shown in FIGS. 8 and 10, a pancreatic cancer patient and a pancreatitis patient can be distinguished by detecting pathological haptoglobin using a fucose α1→6 specific lectin in an individual having a higher amount of CA 19-9 than a healthy individual.

Figure 11:
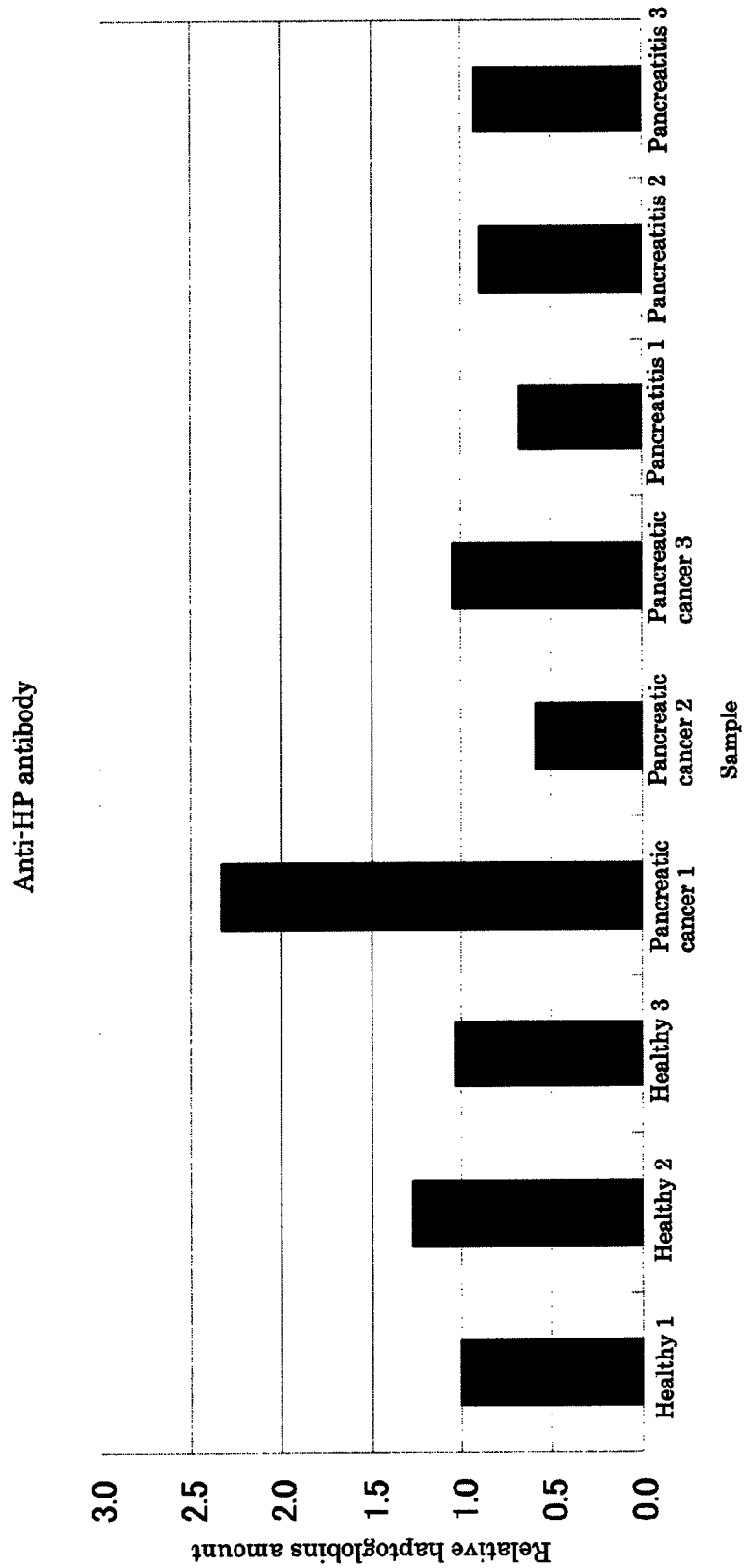
FIG. 11 shows the relative amount of haptoglobin in serum calculated from the binding studies with anti-haptoglobin antibody (Anti-HP antibody).

The amount of haptoglobin was also measured using anti-haptoglobin antibody instead of then lectin. Relative values which are normalized such that the reaction value (absorbance) for Healthy 1 was set to 1 are shown as the relative amount of haptoglobin (Relative HP amount) in FIG. 11. Furthermore, "absorbance/Relative HP amount" was calculated by dividing the reaction values (absorbance) in FIGS. 8 and 9 by Relative HP amount. "Absorbance/Relative HP amount" means the relative degree of fucosylation of haptoglobin in each sample. Results are shown in FIGS. 12 and 13.

As shown in FIGS. 12 and 13, it is clear that PTL can detect the changes in the sugar chains of haptoglobin as a normal cell becomes a pancreatic cancer cell more accurately than the conventional lectins. Absorbance/Relative HP amount is expected to be an indicator of the clinical stage of pancreatic cancer, since it also represents the degree of fucosylation of haptoglobin. Thus, pancreatic cancer can also be detected by the amount of pathological haptoglobin per haptoglobin, detected using a fucose α1→6 specific lectin.

From the results above, it is clear that pancreatic cancer can be detected by measuring pathological haptoglobin using PTL. In the canceration process of a normal cell to pancreatic cancer, PTL can detect pathological haptoglobin as a tumor marker, more accurately than the previously known fucose α1→6 specific lectins. Due to its high specificity, PTL can likely detect a target fucose α1→6 sugar-chain compound in a mixture of a fucose α1→6 sugar-chain compound and other sugar-chain compounds more accurately than the other lections. Furthermore, pancreatic cancer can be discriminated from pancreatitis by combining the detection of pathological haptoglobin using PTL and the detection of another tumor marker CA 19-9 which shows a higher value in an individual with pancreatic disease than in a healthy individual. It can be employed for a diagnostic reagent or a diagnostic reagent kit for pancreatic cancer or pancreatitis, the reagent or the kit being based on the interaction between PTL and a sugar chain.

What is claimed is:

1. A method of detecting pancreatic cancer, comprising:
collecting a sample from a living body of a suspected patient;
contacting a fucose α1→6 specific lectin to the sample in order to be allowed to act on pathological haptoglobin present in the sample obtained from the living body and obtain a lectin-pathological haptoglobin complex, said lectin:
(1) being extracted from basidiomycetes,
(2) having a molecular weight of 4,000 to 40,000 as determined by the SDS polyacrylamide gel electrophoresis,
(3) having affinity for fucose α1→6 sugar chains with a binding constant of $1.0 \times 10^4 \text{ M}^{-1}$ or more at 25° C., and
(4) having a binding constant $1.0 \times 10^3 \text{ M}^{-1}$ or less at 25° C. for a high mannose sugar chain, which is an asparagine-linked sugar chain wherein a chitobiose core is bound to five to nine mannose residues, and/or a glycolipid which does not contain a fucose α1→6 sugar chain; and
determining the lectin-pathological haptoglobin complex by an assay selected from the group consisting of ELISA, lectin chromatography, lectin blotting, lectin staining, lectin chip, a condensation method and a surface plasmon resonance method to detect the occurrence of the pancreatic cancer.

2. The method of detecting pancreatic cancer according to claim 1, wherein said basidiomycete belongs to Strophariaceae, Tricholomataceae, Amanitaceae or Polyporaceae.

3. The method of detecting pancreatic cancer according to claim 2, wherein said basidiomycete is *Pholiota terrestris* Overholts, *Pholiota squarrosa*, *Pholiota aurivella*, *Stropharia rugosoannulata*, *Naematoloma sublateritium*, *Lepista sordida* or *Amanita muscaria*.

4. The method of detecting pancreatic cancer according to claim 1, wherein said sample is human serum or plasma.

5. The method of detecting pancreatic cancer according to claim 1, wherein the pathological haptoglobin is detected using said fucose α1→6 specific lectin, and one or more lectins or antibodies.

6. The method of detecting pancreatic cancer according to claim 1 wherein the pathological haptoglobin is detected by an assay using fucose α1→6 specific lectins and anti-haptoglobin antibodies.

7. The method of detecting pancreatic cancer according to claim 1, wherein said fucose α1→6 specific lectin is labeled.

8. A method of detecting pancreatic cancer or pancreatitis, comprising:
  collecting a sample from a living body of a suspected patient having 30 U/mL or more of tumor marker CA 19-9 in serum;
  contacting a fucose α1→6 specific lectin to the sample in order to be allowed to act on pathological haptoglobin present in the sample obtained from the living body and obtain a lectin-pathological haptoglobin complex, said lectin:
    (1) being extracted from basidiomycetes,
    (2) having a molecular weight of 4,000 to 40,000 as determined by the SDS polyacrylamide gel electrophoresis,
    (3) having affinity for fucose α1→6 sugar chains with a binding constant of $1.0 \times 10^4$ $M^{-1}$ or more at 25° C., and
    (4) having a binding constant of $1.0 \times 10^3$ $M^{-1}$ or less at 25° C. for a high mannose sugar chain, which is an asparagine-linked sugar chain wherein a chitobiose core is bound to five to nine mannose residues, and/or a glycolipid which does not contain a fucose α1→6 sugar chain; and
  determining the lectin-pathological haptoglobin complex by an assay selected from the group consisting of ELISA, lectin chromatography, lectin blotting, lectin staining, lectin chip, a condensation method and a surface plasmon resonance method to detect the occurrence of the pancreatic cancer.

9. The method of detecting pancreatic cancer or pancreatitis according to claim 8, wherein said basidiomycete belongs to Strophariaceae, Tricholomataceae, Amanitaceae or Polyporaceae.

10. The method of detecting pancreatic cancer or pancreatitis according to claim 9, said basidiomycete is *Pholiota terrestris* Overholts, *Pholiota squarrosa, Pholiota aurivella, Stropharia rugosoannulata, Naematoloma sublateritium, Lepista sordida* or *Amanita muscaria*.

11. The method of detecting pancreatic cancer or pancreatitis according to claim 8, wherein said sample is human serum or plasma.

12. The method of detecting pancreatic cancer or pancreatitis according to claim 8, wherein the pathological haptoglobin is detected using said fucose α1→6 specific lectin, and one or more lectins or antibodies.

13. The method of detecting pancreatic cancer or pancreatitis according to claim 8, wherein the pathological haptoglobin is detected by an assay using said fucose α1→6 specific lectin and anti-haptoglobin antibody.

14. The method of detecting pancreatic cancer or pancreatitis according to claim 8, wherein said fucose α1→6 specific lectin is labeled.

15. A diagnostic reagent or kit for detecting pancreatic cancer and/or pancreatitis, comprising:
  a fucose α1→6 specific lectin, said lectin:
    (1) being extracted from basidiomycetes,
    (2) having a molecular weight of 4,000 to 40,000 as determined by the SDS polyacrylamide gel electrophoresis,
    (3) having affinity for fucose α1→6 sugar chains with a binding constant of $1.0 \times 10^4$ $M^{-1}$ or more at 25° C., and
    (4) having a binding constant of $1.0 \times 10^3$ $M^{-1}$ or less at 25° C. for a high mannose sugar chain, which is an asparagine-linked sugar chain wherein a chitobiose core is bound to five to nine mannose residues, and/or a glycolipid which does not contain a fucose α1→6 sugar chain; and
  an anti-haptoglobin antibody.

16. The diagnostic reagent or kit for detecting pancreatic cancer and/or pancreatitis according to claim 15, further comprising anti-CA 19-9 antibody.

* * * * *